(12) United States Patent
Dewal

(10) Patent No.: US 11,753,676 B2
(45) Date of Patent: Sep. 12, 2023

(54) MULTIPLEXED IN SITU HYBRIDIZATION OF TISSUE SECTIONS FOR SPATIALLY RESOLVED TRANSCRIPTOMICS WITH EXPANSION MICROSCOPY

(71) Applicant: EXPANSION TECHNOLOGIES, Boston, MA (US)

(72) Inventor: Mahender Babu Dewal, Arlington, MA (US)

(73) Assignee: EXPANSION TECHNOLOGIES, Cambridge, MA (US)

(*) Notice: Subject to any disclaimer, the term of this patent is extended or adjusted under 35 U.S.C. 154(b) by 212 days.

(21) Appl. No.: 16/755,274

(22) PCT Filed: Oct. 10, 2018

(86) PCT No.: PCT/US2018/055254
§ 371 (c)(1),
(2) Date: Apr. 10, 2020

(87) PCT Pub. No.: WO2019/075091
PCT Pub. Date: Apr. 18, 2019

(65) Prior Publication Data
US 2020/0239946 A1  Jul. 30, 2020

Related U.S. Application Data

(60) Provisional application No. 62/571,076, filed on Oct. 11, 2017.

(51) Int. Cl.
C12P 19/34 (2006.01)
C12Q 1/6841 (2018.01)

(52) U.S. Cl.
CPC ..... *C12Q 1/6841* (2013.01); *C12Q 2525/301* (2013.01); *C12Q 2527/125* (2013.01); *C12Q 2563/107* (2013.01)

(58) Field of Classification Search
USPC .............. 435/6.1, 7.1, 6.11, 6.12, 91.1, 91.2, 435/91.51, 287.1, 287.2; 436/94, 501; 536/23.1, 24.3, 24.33
See application file for complete search history.

(56) References Cited

U.S. PATENT DOCUMENTS

| | | |
|---|---|---|
| 8,911,942 B2 | 12/2014 | Mohammed et al. |
| 10,309,879 B2 | 6/2019 | Chen et al. |
| 2010/0291152 A1 | 11/2010 | Shone et al. |
| 2015/0267251 A1 | 9/2015 | Cai et al. |
| 2016/0116384 A1 | 4/2016 | Chen et al. |
| 2017/0009278 A1 | 1/2017 | Söderberg et al. |

(Continued)

FOREIGN PATENT DOCUMENTS

| | | |
|---|---|---|
| WO | WO2017/139501 | 8/2017 |
| WO | WO2017/143317 | 8/2017 |

OTHER PUBLICATIONS

Atta et al., "Swelling Behaviors of Polyelectrolyte Hydrogels Containing Sulfonate Groups"; Polym. Adv. Technol., 2002, vol. 13, pp. 567-576.

(Continued)

*Primary Examiner* — Frank W Lu
(74) *Attorney, Agent, or Firm* — Mark S. Cohen; PEARL COHEN ZEDEK LATZER BARATZ LLP

(57) ABSTRACT

This invention relates to imaging, such as by expansion microscopy, labelling, and analyzing biological samples, such as cells and tissues, as well as reagents and kits for doing so.

31 Claims, 9 Drawing Sheets

(56) References Cited

U.S. PATENT DOCUMENTS

2017/0067096 A1 3/2017 Wassie et al.
2017/0253918 A1 9/2017 Kohman

OTHER PUBLICATIONS

Chen et al., "Expansion microscopy"; Science, Jan. 30, 2015, vol. 347(6221): pp. 543-548.
Chen et al., "Supplementary Material for Expansion Microscopy"; Science Express DOI: 10.1126/science. 1260088, Jan. 15, 2015, 18 pages.
Le Goff et al., "Hydrogel microparticles for biosensing"; European. Polymer Journal, 2015, vol. 72, pp. 386-412.
Maruani et al., "A plug-and-play approach to antibody-based therapeutics via a chemoselective dual click strategy"; Nature Communications, 2015, 6:6645 doi: 10.1038/ncoms7645.
Okay, O., "General Properties of Hydrogels", Hydrogel Sensors and Actuators, 2009, G. Gerlach and K.-F. Arndt (eds.), Springer Series on Chemical Sensors and Biosensors 6, Springer-Verlag Berlin Heidelberg 2009 (15 pages).
Skouri et al., "Swelling and Elastic Properties of Polyelectrolyte Gels", Macromolecules, 1995, vol. 28, pp. 197-210.
Wahlby et al., "Sequential Immunofluorescence Staining and Image Analysis for Detection of Large Numbers of Antigens in Individual Cell Nuclei"; Cytometry, 2002, vol. 47, pp. 32-41.
International Search Report and Written Opinion, dated Dec. 27, 2018, from corresponding International Application No. PCT/US2018/055254, filed Oct. 10, 2018.

MULTIPLEXED IN SITU HYBRIDIZATION OF TISSUE SECTIONS FOR SPATIALLY RESOLVED TRANSCRIPTOMICS WITH EXPANSION MICROSCOPY

CROSS-REFERENCE TO RELATED APPLICATIONS

This application is a National Phase Application of PCT International Application No. PCT/US2018/055254, with an International Filing Date of Oct. 10, 2018, which claims priority of U.S. Provisional Application No. 62/571,076, filed Oct. 11, 2017, both of which are hereby incorporated by reference.

FIELD OF THE INVENTION

The invention relates to imaging, such as by expansion microscopy, labelling, and analyzing biological samples, such as cells and tissues, as well as reagents and kits for doing so.

BACKGROUND OF THE INVENTION

Understanding the transcriptional states and spatial organization of ribonucleic acid (RNA) within tissues is essential to determining the mechanisms of disease and for answering a multitude of scientific questions. However, the imaging of RNA is still limited due to diffraction-limited resolutions on conventional microscopes which reduce the accuracy of RNA expression level quantification and due to the limited number of transcripts which can be resolved within a single specimen. Current imaging technologies for transcriptional profiling of complex tissues include confocal microscopy or super-resolution microscopy of RNA in situ hybridization targets, either via RNA fluorescence in situ hybridization (FISH) (e.g., Chaumeil et al., "Combined Immunofluorescence, RNA Fluorecent In Situ Hybridization, and DNA Fluorescent In Situ Hybridization to Study Chromatin Changes, Transcriptional Activity, Nuclear Organization, and X-Chromosome Inactivation" (ch. 18, pp. 297-308) in R. Hancock (ed), *The Nucleus: Vol. 1: Nuclei and Subnuclear Components* [Humana Press 2008]), or via RNA hybridization chain reaction (HCR) (e.g., Dirks & Pierce, *Proc. Natl. Acad. Sci.* [2004] 101(43): 15275; U.S. Pat. Nos. 7,727,721 [2010], 8,124,751 [2012], and 8,507,204 [2013]; Choi et al., *ACS Nano.* [2014] 8(5): 4284-4294; Shah et al., *Development* [2016] 143:2862). Although super-resolution techniques can provide improved spatial resolution, they are slow and require ultra-thin section of specimens.

In expansion microscopy (ExM), 3-dimensional imaging with nanoscale precision is performed on cells and tissues. This is accomplished by physically expanding the biological sample using a dense polymer matrix. The first step of this process involves treating the tissue with a fluorescent protein-binding-group (typically an antibody or/and antibody-oligonucleotide conjugate) that selectively binds to the protein being analyzed. Next the sample is infused with a monomer solution that permeates into the tissue. Free radical polymerization of this solution creates a polymer network that is physically connected to the protein-binding-groups through customized bioconjugation chemistry. Lastly, the tissue is digested and the hydrogel (and fluorescent dyes) expands uniformly. The result is a polymer network that contains fluorescent dyes where the target proteins were located. This process has many advantages. Notably, it allows pseudo super-resolution imaging with conventional confocal microscopy because the imaging targets are no longer diffraction limited. Additionally, the tissue digestion clears the sample allowing imaging deep into thick tissues samples. (See, e.g., LeGoff et al., *Eur. Polym. J.* [2015] http://dx.doi.org/10/1016/j.eurpolymj.2015.02.022)

Critical to the success of the ExM process is the ability to physically connect the fluorescent protein-binding-groups to the polymer network. Current ExM attachment chemistry uses a trifunctional, double-stranded DNA linker to accomplish this. Because the tissue digestion enzymes are also capable of digesting the antibodies typically used as protein-binding-groups, the fluorescent dyes must be attached to the DNA and not the antibody. Also needed is the presence of a chemical group that can polymerize into the gel matrix. Current examples of ExM use a chemical arrangement in which one strand of DNA is connected to the protein-binding-group while the complementary strand possesses both the dye and the polymerizable group. Using this strategy, cells and brain tissue were successfully stained with up to 3 different protein-binding-groups, expanded, and imaged (Chen et al., *Science* 347:543 [2015]; Chen et al., "Nanoscale Imaging of RNA with Expansion Microscopy," *Nature Methods* 13:679 [2016]). However, because the number of fluorescent dyes that can be used is small (typically <6), this strategy is limited to imaging only a small number of proteins per sample. Additionally, the polymerization process dampens the fluorescence of the dyes, which are permanently connected to the gel matrix. By rearranging the location of the three chemical groups (dye, gel binding group, and protein-binding-group) on the DNA linker, previous limitations in protein imaging some previous limitations have been overcome.

However, use of DNA/antibody conjugates has also had several disadvantages. Buffers with uncommon additives are necessary in order to prevent the DNA on the antibody from binding to the nuclear DNA in the sample. Also, the presence of the DNA on the antibody reduces the extent and the rate at which it binds to the target. The result is that the current ExM processes are lengthy, and the staining is commonly dim compared to controls, making this approach unsuitable for RNA detection due to the limited number of transcripts which can be resolved within a single specimen.

Alternatively, attempts have been made to overcome problems of ExM with respect to dim staining by utilizing an improved bioconjugation strategy or by utilizing turbo-expansion microscopy (TurboExM), which does not use DNA as a linker, and samples could be stained brightly and more rapidly than using previous ExM processes. Turbo-ExM relies on antibodies, which can be directly acrylated (and hence suitable for polymerization), either before, after, or at the same time as attachment with a detectable label, but also that the detectable label will remain after the tissue digestion step, which is necessary for ExM. However, this approach allows only protein detection and is less suitable for RNA detection or imaging both proteins and nucleic acids. (see *Nat Biotechnology* [2016] 34 (9), 987-992)

The interrogation of RNA in a highly multiplexed and efficient manner with spatial information remains a challenge in structural biology and medicine.

Surprisingly, it has been found that by combining serial RNA hybridization strategies with ExM, it is possible to read multiplexed RNA transcript data from thick high resolution tissue specimens. This approach allows for high speed transcriptional profiling of a large number of genes across thick tissue sections.

SUMMARY OF THE INVENTION

In one aspect, provided herein are methods of labeling nucleic acids and proteins together in a biological sample, said method comprising: (a) contacting the sample with a first gel binding moiety and a second gel binding moiety under conditions wherein the first gel binding moiety operably links to proteins in the sample and the second gel binding moiety operably links to nucleic acids in the sample; (b) contacting the sample with a solution comprising monomers of a polyelectrolyte gel; (c) by free radical polymerization, polymerizing said monomers to form the polyelectrolyte gel and covalently conjugating the first and second gel binding moieties to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (g) contacting the sample with the plurality of initiator DNA probes under conditions wherein the sequence complementary to the sequence from one of the nucleic acid targets of interest hybridizes to that sequence from the nucleic acid target of interest; (h) for each initiator DNA probe, providing a pair of fluorophore-labeled DNA hairpins that metastably co-exist in the absence of the initiator DNA probe; and (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe.

In another aspect, provided herein are methods of labeling a biological sample comprising a ribonucleic acid (RNA) target of interest, said methods being performed under RNAse-free conditions and said methods comprising: (a) contacting the sample with a gel binding moiety under conditions wherein the gel binding moiety operably links to RNA in the sample; (b) contacting the sample with a solution comprising monomers of a polyelectrolyte gel; (c) by free radical polymerization, polymerizing said monomers to form the polyelectrolyte gel and covalently conjugating the gel binding moiety to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (g) contacting the sample with the plurality of initiator DNA probes under conditions wherein the sequence complementary to the sequence from one of the RNA targets of interest hybridizes to that sequence from the RNA target of interest; (h) for each initiator DNA probe, providing a pair of fluorophore-labeled DNA hairpins that metastably co-exist in the absence of the initiator DNA probe; and (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe.

In another aspect, provided herein are methods of imaging nucleic acids and proteins together in a biological sample, said method comprising: (a) contacting the sample with a first gel binding moiety and a second gel binding moiety under conditions wherein the first gel binding moiety operably links to proteins in the sample and the second gel binding moiety operably links to nucleic acids in the sample; (b) contacting the sample with a solution comprising monomers of a polyelectrolyte gel; (c) by free radical polymerization, polymerizing said monomers to form the polyelectrolyte gel and covalently conjugating the first and second gel binding moieties to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (g) contacting the sample with the plurality of initiator DNA probes under conditions wherein the sequence complementary to the sequence from one of the nucleic acid targets of interest hybridizes to that sequence from the nucleic acid target of interest; (h) for each initiator DNA probe, providing a pair of fluorophore-labeled DNA hairpins that metastably co-exist in the absence of the initiator DNA probe; (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; and (j) obtaining an image of the sample.

In another aspect, provided herein are methods of imaging ribonucleic acid (RNA) in a biological sample, said method being performed under RNAse-free conditions and said method comprising: (a) contacting the sample with a gel binding moiety under conditions wherein the gel binding moiety operably links to RNA in the sample; (b) contacting the sample with a solution comprising monomers of a polyelectrolyte gel; (c) by free radical polymerization, polymerizing said monomers to form the polyelectrolyte gel and covalently conjugating the gel binding moiety to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (g) contacting the sample with the plurality of initiator DNA probes under conditions wherein the sequence complementary to the sequence from one of the RNA targets of interest hybridizes to that sequence from the RNA target of interest; (h) for each initiator DNA probe, providing a pair of fluorophore-labeled DNA hairpins that metastably co-exist in the absence of the initiator DNA probe; (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; and (j) obtaining an image of the sample.

In another aspect, provided herein are methods of imaging nucleic acids and proteins together in a biological sample, said method comprising: (a) contacting the sample with a first gel binding moiety and a second gel binding moiety under conditions wherein the first gel binding moiety operably links to proteins in the sample and the second gel binding moiety operably links to nucleic acids in the sample; (b) contacting the sample with a solution comprising monomers of a polyelectrolyte gel; (c) by free radical polymerization, polymerizing said monomers to form the polyelectrolyte gel and covalently conjugating the first and second gel binding moieties to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (g) contacting the sample with the plurality of initiator DNA probes under conditions wherein the sequence complementary to the sequence from one of the nucleic acid targets of interest hybridizes to that sequence from the nucleic acid target of interest; (h) for each initiator DNA probe, providing a pair of fluorophore-labeled DNA hairpins that metastably co-exist in the absence of the initiator DNA probe; (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; (j) obtaining an image of the sample; (k) treating the sample with a deoxyribonuclease to remove the initiator DNA probes and amplification polymers; and (l) repeating steps (f)-(k) one or more times for additional RNA targets of interest.

In another aspect, provided herein are methods of imaging ribonucleic acid (RNA) in a biological sample, said method being performed under RNAse-free conditions and said method comprising: (a) contacting the sample with a gel binding moiety under conditions wherein the gel binding moiety operably links to RNA in the sample; (b) contacting the sample with a solution comprising monomers of a polyelectrolyte gel; (c) by free radical polymerization, polymerizing said monomers to form the polyelectrolyte gel and covalently conjugating the gel binding moiety to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (g) contacting the sample with the plurality of initiator DNA probes under conditions wherein the sequence complementary to the sequence from one of the RNA targets of interest hybridizes to that sequence from the RNA target of interest; (h) for each initiator DNA probe, providing a pair of fluorophore-labeled DNA hairpins that metastably co-exist in the absence of the initiator DNA probe; (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; (j) obtaining an image of the sample; (k) treating the sample with a deoxyribonuclease to remove the initiator DNA probes and amplification polymers; and (l) repeating steps (f)-(k) one or more times for additional RNA targets of interest.

In another aspect, provided herein are compounds comprising

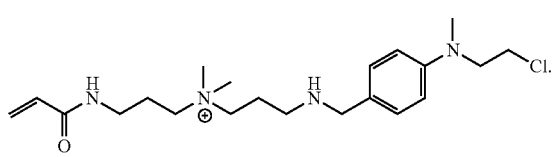 [SMILES: C=CC(=O)NCCC[N+](C)(C)CCCNCc1ccc(N(C)CCCl)cc1]

In another aspect, provided herein are compositions comprising

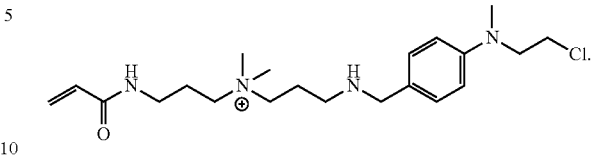

In another aspect, provided herein are additional methods, as well as reagents (e.g., the binding compositions, labels nucleic acid probes) and kits for use in the methods described herein. For example, provided herein are methods for embedding a sample in a polyacrylamide gel matrix using a borate buffer.

Other features and advantages of this invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of this specification and are included to further demonstrate certain aspects of this disclosure, the inventions of which can be better understood by reference to one or more of these drawings in combination with the detailed description of specific embodiments presented herein.

DETAILED DESCRIPTION OF THE INVENTION

Figure 1A:
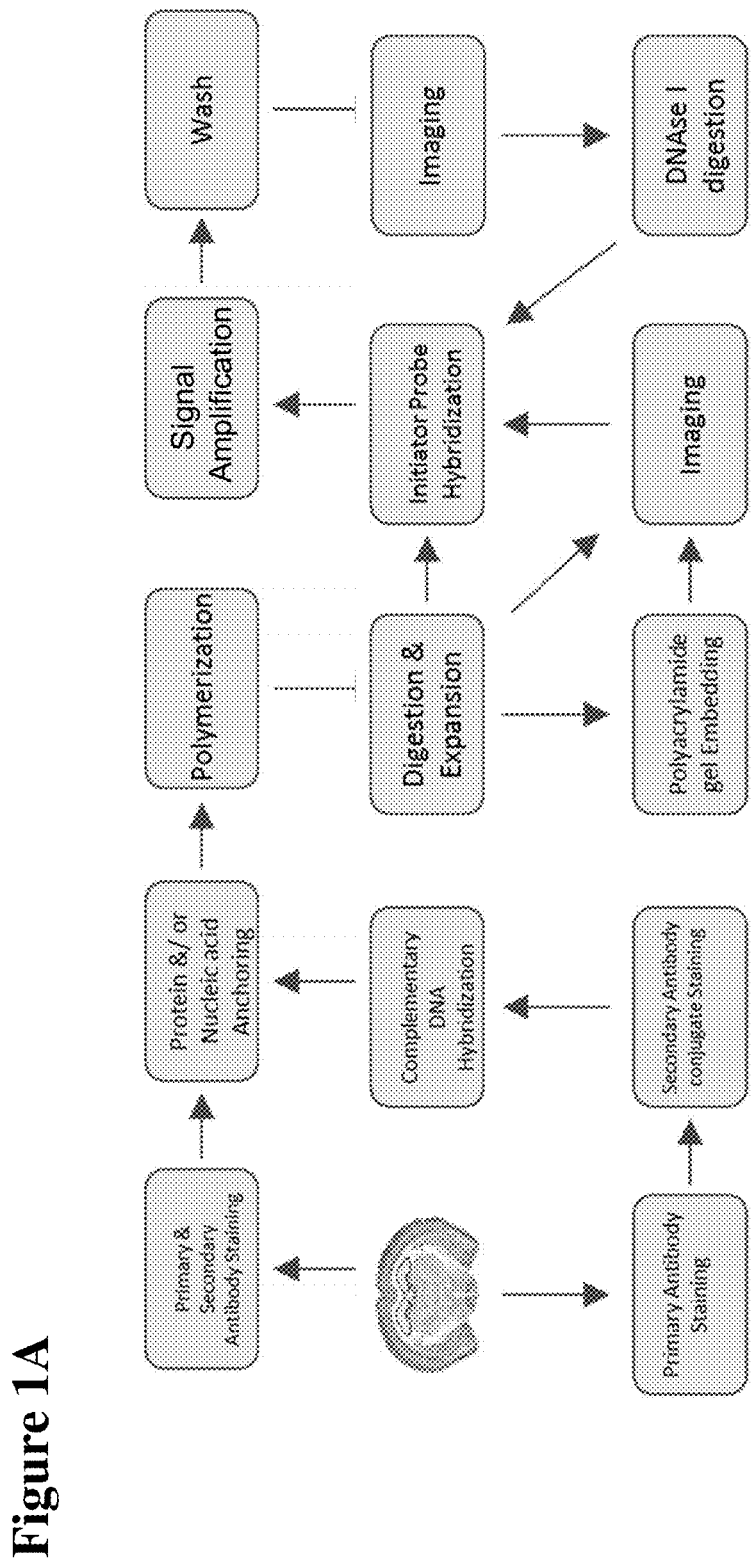
FIGS. 1A-1B. Schematic depictions of serial hybridization and removal of multiple (n-number) probes.

In aspects of this invention, the technique of expansion microscopy (ExM) is employed in order to spatially resolve multiplexed super-resolution ribonucleic acid (RNA) targets within cleared tissue samples. In ExM, biological samples are permeated with a solution of water soluble small-molecule monomers which are polymerized into a swellable hydrogel that can expand upon addition of water, allowing for an enhancement in spatial resolution and specimen clearing. The tissues are then stained for RNA genes of interest, imaged, and denatured to displace the probes. The tissues can then be re-stained for new RNA genes, thereby facilitating serial labeling and readout of a large number of probes in a single sample across thick specimen regions. This, in turn, allows for effective transcriptional profiling of thousands of genes across entire complex tissues.

In ExM, 3-dimensional imaging with nanoscale precision is performed on cells and tissues. This is accomplished by physically expanding the biological sample using a dense polymer matrix.

In some embodiments, methods are provided to anchor native nucleic acids within fresh frozen tissue sections and to perform the ExM procedure to physically expand the specimens, to employ hybridization chain reaction (HCR) signal amplification in order to obtain high signal-to-noise puncta readout, and optionally, to use DNAse I to dislocate and wash out the initiator probes and rehybridize new probes for serial hybridization.

In some embodiments, the sample is contacted with a gel binding moiety that operably links (typically covalently) to RNA in the sample. Next the sample is infused with a monomer solution that permeates into the tissue. Free radical polymerization of this solution creates a polymer network that is covalently conjugated to the gel binding moiety, (optionally also physically connected to protein-binding-groups either through a linker molecule or a customized bioconjugation chemistry). The sample is then digested and the hydrogel expands uniformly. Then, the sample is treated with an RNA-binding-group (typically a single-stranded nucleic acid, such as a deoxyribonucleic acid [DNA] primer) that selectively binds to the RNA being analyzed, and then labeled (typically fluorescently) by HCR amplification. The result is a polymer network that contains fluorescent dyes where the target RNAs are (and optionally also where target proteins were) located. This process has many advantages. Notably, it allows pseudo super resolution imaging with conventional confocal microscopy because the imaging targets are no longer diffraction limited. Additionally, the tissue digestion clears the sample allowing imaging deep into thick tissues samples.

Significant to the success of the ExM process, as used in embodiments for protein detection, has been the ability to physically connect the fluorescent protein-binding-groups to the polymer network. In one example, ExM attachment chemistry uses a trifunctional, double-stranded DNA linker to accomplish this. Because the tissue digestion enzymes are also capable of digesting the antibodies typically used as protein-binding-groups, it has been understood that fluorescent dyes must be attached to the DNA and not the antibody. Also needed is the presence of a chemical group that can polymerize into the gel matrix (e.g., a methacrylamide group) on the DNA. In another example, proteins and antibodies are directly linked to the polymer network using a linker molecule (Acryloyl-X (6-((acryloyl)amino) hexanoic acid succinimidyl ester)) with a methacrylamide group.

In some embodiments, the ExM process uses a chemical arrangement in which one strand of DNA (the probe) is connected to the RNA while a mismatched tail sequence of the probe DNA is hybridized to a second, complementary DNA fragment that possesses both the dye and the polymerizable group. This approach focuses on the number of dyes intended for analytical use.

Alternative bioconjugation strategies can be utilized. The locations of the three necessary chemical groups (dye, gel binding group, and RNA-binding-group) on the DNA probe and on the second, complementary DNA can be rearranged.

In other embodiments, the dye is not attached to the same DNA strand as the gel binding group. The consequence is that the final polymer matrix is physically connected to a strand of DNA with a defined sequence (and no dye). Whereas one embodiment replaces the target RNA with a dye that can be imaged, this embodiment replaces the target RNA with a DNA barcode. This barcode can be decoded in a subsequent step using multiplexed fluorescence in situ hybridization (FISH) which is not limited by the number of available fluorescent dyes. This modification in chemistry can allow the simultaneous tagging of many proteins in the same sample because each protein can be given a unique barcode. The small number of dyes is not limiting and the maximum number of RNA targets that can be imaged is limited now by the number of available DNA primers. Additionally, because the DNA strand attached to the dye is not bound to the polymer matrix, the loss in fluorescence observed during polymerization is irrelevant because the dye-containing strand can be removed. Imaging of the barcode can be done later with FISH. In one embodiment of this approach, the DNA probe hybridized to an RNA target has a tail comprising the dye, while the second DNA sequence complementary to the tail is attached to the gel binding group. In another embodiment of this approach, the DNA probe hybridized to the RNA target has a tail comprising the gel binding group, while a second DNA sequence complementary to the tail is attached to the dye.

In one aspect, provided herein are methods of labeling nucleic acids and proteins together in a biological sample, said method comprising: (a) contacting the sample with a first gel binding moiety and a second gel binding moiety under conditions wherein the first gel binding moiety operably links to proteins in the sample and the second gel binding moiety operably links to nucleic acids in the sample; (b) contacting the sample with a solution comprising monomers of a polyelectrolyte gel; (c) by free radical polymerization, polymerizing said monomers to form the polyelectrolyte gel and covalently conjugating the first and second gel binding moieties to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (g) contacting the sample with the plurality of initiator DNA probes under conditions wherein the sequence complementary to the sequence from one of the nucleic acid targets of interest hybridizes to that sequence from the nucleic acid target of interest; (h) for each initiator DNA probe, providing a pair of fluorophore-labeled DNA hairpins that metastably co-exist in the absence of the initiator DNA probe; and (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe. In some embodiments, the methods further comprising, prior to step (a), the steps of: (I) contacting the sample with at least one primary antibody under conditions where it selectively recognizes a target protein of interest; and (II) contacting the sample with at least one secondary antibody operably linked to a detectable label.

In another aspect, provided herein are methods of labeling a biological sample comprising a ribonucleic acid (RNA) target of interest, said methods being performed under RNAse-free conditions and said methods comprising: (a) contacting the sample with a gel binding moiety under conditions wherein the gel binding moiety operably links to RNA in the sample; (b) contacting the sample with a solution comprising monomers of a polyelectrolyte gel; (c) by free radical polymerization, polymerizing said monomers to form the polyelectrolyte gel and covalently conjugating the gel binding moiety to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (g) contacting the sample with the plurality of initiator DNA probes under conditions wherein the sequence complementary to the sequence from one of the RNA targets of interest hybridizes to that sequence from the RNA target of interest; (h) for each initiator DNA probe, providing a pair of fluorophore-labeled DNA hairpins that metastably co-exist in the absence of the initiator DNA probe; and (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe.

In another aspect, provided herein are methods of imaging nucleic acids and proteins together in a biological sample, said method comprising: (a) contacting the sample with a first gel binding moiety and a second gel binding moiety under conditions wherein the first gel binding moiety operably links to proteins in the sample and the second gel binding moiety operably links to nucleic acids in the sample; (b) contacting the sample with a solution comprising monomers of a polyelectrolyte gel; (c) by free radical polymerization, polymerizing said monomers to form the polyelectrolyte gel and covalently conjugating the first and second gel binding moieties to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (g) contacting the sample with the plurality of initiator DNA probes under conditions wherein the sequence complementary to the sequence from one of the nucleic acid targets of interest hybridizes to that sequence from the nucleic acid target of interest; (h) for each initiator DNA probe, providing a pair of fluorophore-labeled DNA hairpins that metastably co-exist in the absence of the initiator DNA probe; (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; and (j) obtaining an image of the sample. In some embodiments, the methods further comprising, prior to step (a), the steps of: (I) contacting the sample with at least one primary antibody under conditions where it selectively recognizes a target protein of interest; and (II) contacting the sample with at least one secondary antibody operably linked to a detectable label.

In another aspect, provided herein are methods of imaging ribonucleic acid (RNA) in a biological sample, said method being performed under RNAse-free conditions and said method comprising: (a) contacting the sample with a gel binding moiety under conditions wherein the gel binding moiety operably links to RNA in the sample; (b) contacting the sample with a solution comprising monomers of a polyelectrolyte gel; (c) by free radical polymerization, polymerizing said monomers to form the polyelectrolyte gel and covalently conjugating the gel binding moiety to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (g) contacting the sample with the plurality of initiator DNA probes under conditions wherein the sequence complementary to the sequence from one of the RNA targets of interest hybridizes to that sequence from the RNA target of interest; (h) for each initiator DNA probe, providing a pair of fluorophore-labeled DNA hairpins that metastably co-exist in the absence of the initiator DNA probe; (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; and (j) obtaining an image of the sample.

In another aspect, provided herein are methods of imaging nucleic acids and proteins together in a biological sample, said method comprising: (a) contacting the sample with a first gel binding moiety and a second gel binding moiety under conditions wherein the first gel binding moiety operably links to proteins in the sample and the second gel binding moiety operably links to nucleic acids in the sample; (b) contacting the sample with a solution comprising monomers of a polyelectrolyte gel; (c) by free radical polymerization, polymerizing said monomers to form the polyelectrolyte gel and covalently conjugating the first and second gel binding moieties to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (g) contacting the sample with the plurality of initiator DNA probes under conditions wherein the sequence complementary to the sequence from one of the nucleic acid targets of interest hybridizes to that sequence from the nucleic acid target of interest; (h) for each initiator DNA probe, providing a pair of fluorophore-labeled DNA hairpins that metastably co-exist in the absence of the initiator DNA probe; (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; (j) obtaining an image of the sample; (k) treating the sample with a deoxyribonuclease to remove the initiator DNA probes and amplification polymers; and (l) repeating steps (f)-(k) one or more times for additional RNA targets of interest. In some embodiments, the methods further comprising, prior to step (a), the steps of: (I) contacting the sample with at least one primary antibody under conditions where it selectively recognizes a target protein of interest; and (II) contacting the sample with at least one secondary antibody operably linked to a detectable label.

In another aspect, provided herein are methods of imaging ribonucleic acid (RNA) in a biological sample, said method being performed under RNAse-free conditions and said method comprising: (a) contacting the sample with a gel binding moiety under conditions wherein the gel binding moiety operably links to RNA in the sample; (b) contacting the sample with a solution comprising monomers of a polyelectrolyte gel; (c) by free radical polymerization, polymerizing said monomers to form the polyelectrolyte gel and covalently conjugating the gel binding moiety to the polyelectrolyte gel; (d) proteolytically digesting said sample; (e) dialyzing said sample to expand said polyelectrolyte gel; (f) providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (g) contacting the sample with the plurality of initiator DNA probes under conditions wherein the sequence complementary to the sequence from one of the RNA targets of interest hybridizes to that sequence from the RNA target of interest; (h) for each initiator DNA probe, providing a pair of fluorophore-labeled DNA hairpins that metastably co-exist in the absence of the initiator DNA probe; (i) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; (j) obtaining an image of the sample; (k) treating the sample with a deoxyribonuclease to remove the initiator DNA probes and amplification polymers; and (l) repeating steps (f)-(k) one or more times for additional RNA targets of interest.

In another aspect, provided herein are compounds comprising

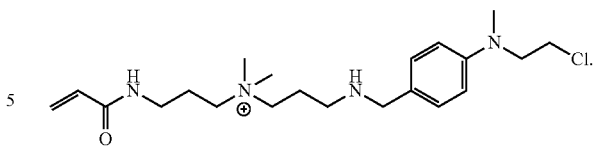

In another aspect, provided herein are compositions comprising

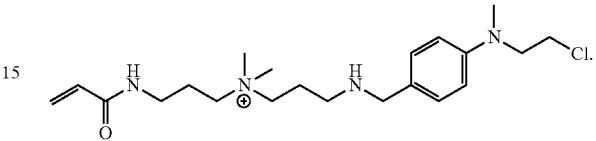

In another aspect, provided herein are additional methods, as well as reagents (e.g., the binding compositions, labels nucleic acid probes) and kits for use in the methods described herein. For example, provided herein are methods for embedding a sample in a polyacrylamide gel matrix using a borate buffer.

In some embodiments, the methods described herein further comprise obtaining an image of the sample. In some embodiments, the image is obtained by confocal microscopy.

With respect to the above methods, compositions, or kits, in some embodiments, the RNA target of interest comprises an mRNA. In some embodiments, the RNA target of interest is an mRNA target of interest and the sequence complementary to a sequence from the mRNA target of interest is at least partially complementary to an exon of said mRNA and at least partially complementary to an intron adjacent to said exon.

With respect to the above methods, an image of the sample may be obtained before expanding the polyelectrolyte gel, as well as after expanding the polyelectrolyte gel.

With respect to the above methods, compositions, or kits, in some embodiments, detectable labels are used (e.g., detectably-labeled DNA hairpins). Examples of detectable labels include, but are not limited to, fluorescent labels or fluorophores. Examples of fluorophores include, but are not limited to, fluorescein isothiocyanate (FITC), tetramethylrhodamine (TRITC), 4',6-diamidino-2-phenylindole (DAPI), or cyanine dye 5 (Cy5), Alexa 488, Alexa 514, Alexa 546, Alexa 594, and Alexa 647. In some embodiments, for a pair of fluorophore-labeled DNA hairpins both hairpins are labeled with the same fluorophore. In some embodiments, for a pair of fluorophore-labeled DNA hairpins each hairpin is labeled with a different fluorophore. In some embodiments, only one of the pair of fluorophore-labeled DNA hairpins is labeled with a fluorophore. Examples of fluorophores used to label DNA hairpins for HCR include, but are not limited to, fluorescein isothiocyanate (FITC), tetramethylrhodamine (TRITC), 4',6-diamidino-2-phenylindole (DAPI), or cyanine dye 5 (Cy5), Alexa 488, Alexa 514, Alexa 546, Alexa 594, and Alexa 647.

With respect to the above methods, compositions, or kits, in some embodiments, detection reagents specific for the detectable labels are provided.

In some embodiments, the methods described herein further comprise the step of: removing the initiator DNA probes unhybridized to the RNA target(s) of interest.

In some embodiments, the initiator DNA probes are preferably between 56 and 60 nucleotides in length. In some embodiments, the fluorophore-labeled DNA hairpins are preferably between 72 and 74 nucleotides in length.

With respect to the above methods, compositions, or kits, in some embodiments, the gel binding moiety is an acryloyl or methacryloyl group. In some embodiments, the gel binding moiety is Acryloyl-X (6-((acryloyl)amino)hexanoic acid succinimidyl ester). In some embodiments, the gel binding moiety comprises:

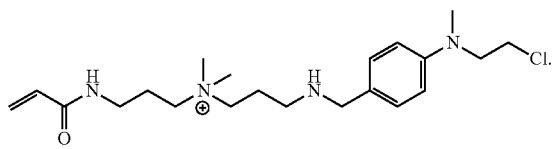 [SMILES: C=CC(=O)NCCC[N+](C)(C)CCCNCc1ccc(N(C)CCCl)cc1]

In some embodiments, the monomer solution comprises sodium acrylate, acrylamide, and N—N'-methylenebisacrylamide. In some embodiments, free radical polymerization is induced with ammonium persulfate (APS) initiator and tetramethylethylenediamine (TEMED).

In some embodiments, the biological sample is chemically fixed and permeabilized prior to step (a) of the methods described herein. In some embodiments, dialyzing the sample to expand the polyelectrolyte gel comprises dialyzing it in water.

With respect to the above methods, compositions, or kits, in some embodiments, the methods further comprise performing the method on a plurality of biological samples in an array or in a microarray. In some embodiments, the array comprises a multiwell plate with each of the plurality of biological samples in a separate well of the multiwell plate. In some embodiments, the multiwell plate comprises a multiwell format of 12, 24, 48, or 96 wells. In some embodiments, said multiwell format comprises a high-throughput multiwell format.

With respect to the above methods or kits, in some embodiments, at least a portion of the method is automated.

With respect to the above methods, compositions, or kits, in some embodiments, the biological sample is derived from a multicellular organism. In some embodiments, the multicellular organism is a vertebrate. In some embodiments, the vertebrate is a mammal or a bird. In some embodiments, the mammal is a human. Alternatively, in some embodiments, the mammal is a non-human mammal. In some embodiments, the biological sample is a brain, heart, lung, gastrointestinal, circulatory, kidney, urogenital, pancreatic, gall bladder, muscle, breast, glandular, or bone sample. In some embodiments, the biological sample comprises serial sections from a single organism, such as a human, and the methods described herein further comprise repeating the method on the serial sections in an array comprising a multiwell plate where each of the serial sections is ordered in a separate well of the plate. Examples of serial sections may include cross-sections or sagittal sections, such as those of an organ, a portion of an organ, a whole organism, or a portion of an organism. An organism includes an embryo. The biological sample may be fresh, frozen, previously mounted, or fresh-frozen.

In some embodiments, the methods described herein further comprise obtaining images of the plurality of serial sections and constructing a three-dimensional model from those images.

With respect to the above methods, compositions, and kits, in some embodiments, the initiator DNA probe has a dissociation constant ($K_D$) less than about $1 \times 10^{-5}$ M, less than about $1 \times 10^{-6}$ M, or less than about $1 \times 10^{-7}$ M. With respect to the above methods, compositions, and kits, in some embodiments, the hairpin molecules have a dissociation constant ($K_D$) less than about $1 \times 10^{-5}$ M, less than about $1 \times 10^{-6}$ M, or less than about $1 \times 10^{-7}$ M.

In some embodiments, the methods further comprise the step of removing the gel binding moieties unconjugated to the polyelectrolyte gel after free radical polymerization.

With respect to methods, in some embodiments, target biomolecules, such as proteins, are detected with antibodies, which include primary and secondary antibodies, or antigen-binding fragments. In some embodiments, the antibodies may be monoclonal or polyclonal antibodies. In some embodiments, the antigen-binding fragments may be derived from polyclonal or monoclonal antibodies. In some embodiments, the antigen-binding fragment is selected from the group consisting of a Fab, a Fab', a (Fab')$_2$, a F(ab')2, a Fv, a single chain antibody (SCA), and a scFv-Fc. In some embodiments, the affinity of the antigen-binding site for the expansion target biomolecule is a high affinity with an affinity constant ($K_a$) greater than $10^4$ M$^{-1}$ or it is between $10^5$-$10^{11}$ M$^{-1}$. A specific binding composition may have a dissociation constant ($K_D$) less than about $1 \times 10^{-5}$ M, less than about $1 \times 10^{-6}$ M, or less than about $1 \times 10^{-7}$ M.

In some embodiments, where preparation of a microarray is concerned, the method also comprises capture element synthesis, preparation of a solid support surface, immobilization of capture elements onto the solid support (e.g., via a robotic arrayer), binding of the target molecule to the immobilized capture elements, and detection and quantification of the target/capture element complex. In some embodiments, at least some part of the method is automated.

Nucleic Acids

As used herein, the terms "polynucleotide" and "nucleic acid molecule" are used interchangeably to refer to polymeric forms of nucleotides of any length, which may have any three-dimensional structure, and may perform any function, known or unknown. The polynucleotides may contain deoxyribonucleotides (DNA), ribonucleotides (RNA), and/or their analogs, including, but not limited to, single-, double-stranded and triple helical molecules, a gene or gene fragment, exons, introns, messenger RNA (mRNA), transfer RNA (tRNA), ribosomal RNA (rRNA), small interfering RNA (siRNA), ribozymes, antisense molecules, complementary DNA (cDNA), genomic DNA (gDNA), recombinant polynucleotides, branched polynucleotides, aptamers, plasmids, vectors, isolated DNA sequences, isolated RNA sequences, nucleic acid probes, peptide nucleic acids (PNA), and primers. A nucleic acid molecule may also comprise modified nucleic acid molecules (e.g., comprising modified bases, sugars, and/or internucleotide linkers).

"Nucleic materials" and "materials from the nucleus" include the nuclear envelope and the contents of the nucleus, including genomic DNA (gDNA) or plasmid DNA. The "non-nucleic acid contents of the nucleus" include the components of the nuclear envelope and any other proteins or other substances of the nucleus that are not nucleic acids.

"Nucleic acids" include deoxyribonucleic acids (DNA) and ribonucleic acids (RNA) of various types, including genomic DNA (gDNA) and messenger RNA (mRNA) and derivatives thereof, such as modified DNA or RNA, including peptide nucleic acids (PNA). "Peptide nucleic acid" (PNA) is a polynucleotide analog in which the sugar-phosphate backbone is replaced by amide bonds. "Genetic material" comprises genomic DNA (gDNA), which is one type of DNA and encodes genetic information, or genetic RNA.

As used herein, a "genetic modification" refers to an addition, deletion or disruption to a cell's normal nucleotides. Art recognized methods include viral mediated gene transfer, liposome mediated transfer, transformation, transfection and transduction. As used herein, a "genetic mutation" is a genetic alteration and is a type of "genetic modification."

As used herein, a "polymorphism" or "genetic polymorphism" is a genetic variation and includes, but is not limited to, a single nucleotide polymorphism (SNP). As used herein, a "genotype" is the genetic composition of an organism, and a "phenotype" is the physical appearance or characteristics of an organism.

A "peptide" is a compound of two or more subunit amino acids, amino acid analogs, or peptidomimetics. The subunits may be linked by peptide bonds or by other bonds (e.g., as esters, ethers, and the like). An "amino acid" refers to either natural and/or unnatural or synthetic amino acids, including glycine and both D or L optical isomers, and amino acid analogs and peptidomimetics. "Amino acids" also includes imino acids. An "oligopeptide" refers to a short peptide chain of three or more amino acids. If the peptide chain is long (e.g., greater than about 10 amino acids), the peptide is a "polypeptide" or a "protein." While the term "protein" encompasses the term "polypeptide," a "polypeptide" may be a less than full-length protein.

As used herein, "expression" refers to the process by which polynucleotides are transcribed into mRNA and/or translated into peptides, polypeptides, or proteins. If the polynucleotide is derived from genomic DNA, expression may, but is not required to, include splicing of the mRNA transcribed from genomic DNA, capping of the 5' end of the mRNA, polyadenylation of the 3' end of the mRNA, or other processing modifications or events.

In some embodiments of the present invention, the ribonucleic acid (RNA) target of interest is a messenger RNA (mRNA).

RNA, including mRNA, is known in the art as being highly susceptible to degradation upon exposure to one or more RNAses. RNAses are present in a wide range of locations, including water, many reagents, laboratory equipment and surfaces, skin, mucous membranes, and elsewhere. It is known in the art that working with RNA generally requires preparing an RNAse-free environment and materials, as well as taking precautions to avoid introducing RNAses into an RNAse-free environment.

RNAse-free precautions are known in the art. These include, but are not limited to, cleaning surfaces with an RNAse cleaning product (e.g., RNASEZAP™ [Ambion] and other commercially available products or 0.5% sodium dodecyl sulfate [SDS] followed by 3% $H_2O_2$); using a designated workspace, materials, and equipment (e.g., pipets, pipet tips); using barrier tips; baking designated glassware (e.g., 300° C. for 2 hours) prior to use; treating enzymes, reagents, and other solutions (e.g., with diethyl pyrocarbonate [DEPC] or dimethyl pyrocarbonate [DMPC]) or using commercially available, certified RNAse-free water or solutions, or ultrafiltered water (e.g., for Tris-based solutions); including an RNAse inhibitor while avoiding temperatures or denaturing conditions that could deactivate the inhibitor); and wearing clean gloves (while avoiding contaminated surfaces) and a clean lab coat. Some solutions (but not Tris-based solutions) can be treated with 0.5 ml DEPC/L, followed by incubation for 2 hours at 37° C., and autoclaving, preferably for at least 45 minutes. Water may be treated with 0.1% v/v DEPC for at least 2 hours at 37° C., then autoclaved. Additional techniques may be useful for procedures in which the RNA is isolated from the sample (e.g., use of TRIZOL™ [Invitrogen] reagents).

RNAses in a biological sample of interest may be inhibited either by rinsing in RNAse-free water and snap freezing the tissue, e.g., in liquid nitrogen, for use at a later date. Alternatively, the biological sample may be stored in ethanol or in an RNAse inhibitor-containing solution at −80° C.

A nucleic acid may have a sequence of at least 65% complementarity; at least 75% complementarity; at least 85% complementarity; at least 95% complementarity; at least 97% complementarity; or at least 99% complementarity to a target or other sequence of interest.

With respect to nucleic acids, "specificity" refers to identity or complementarity as a function of competition or recognition/binding, respectively. "Specificity" of recognition or binding may be affected by the conditions under which the recognition or binding takes place (e.g., pH, temperature, salt concentration, and other factors known in the art) to effect "hybridization" of one nucleic acid domain to another (see, e.g., Wetmur, "DNA Probes: Applications of the Principles of Nucleic Acid Hybridization," *Critical Reviews in Biochemistry and Molecular Biology* 26(3/4): 227-259 (1991)). It is understood that a practitioner may vary conditions without undue experimentation. For example, the practitioner may calculate the melting temperature of a DNA complex, an RNA complex, or a DNA/RNA hybrid complex and adjust conditions accordingly.

"Conservatively modified variants" of sequences may also be envisioned. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed base and/or deoxyinosine or other modified residues. Alternatively, one or more amino acids may be substituted with an amino acid having a similar structure, activity, charge, or other property. Conservative substitution tables providing functionally similar amino acids are well-known in the art (see, e.g., *Proc. Natl. Acad. Sci. USA* 89: 10915-10919 (1992)).

As used herein, "expression" refers to the process by which polynucleotides are transcribed into mRNA and/or translated into peptides, polypeptides, or proteins. If the polynucleotide is derived from genomic DNA, expression may include, but is not required to include, splicing of the mRNA transcribed from the genomic DNA, capping of the 5' end of the mRNA, polyadenylation of the 3' end of the mRNA, or other processing modifications or events.

Where an RNA target of interest is specifically an mRNA in the process of being transcribed or newly transcribed (but prior to the step of intron-splicing during post-transcriptional processing), such as when a practitioner is interested in changes in levels of transcription (e.g., in response to a particular stimulus) in an organism, the initiator DNA probes can be constructed to bridge an exon-intron boundary in the unprocessed mRNA sequence. For example, by using a probe that hybridizes partially to an exon of the mRNA target and partially to an intron adjacent to the exon, such that the probe domain overlaps the exon-intron boundary (i.e., the probe domain hybridizes to an exon sequences adjacent to the exon-intron boundary and intron sequences adjacent to the exon sequences at the exon-intron boundary).

Antibodies and Antigens

As used herein, the term "antibody" encompasses the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, C$\gamma$1, C$\gamma$2, and C$\gamma$3. In each pair, the light and heavy chain variable regions ($V_L$ and $V_H$) are together responsible for binding to an antigen, and the constant regions ($C_L$, C$\gamma$1, C$\gamma$2, and C$\gamma$3, particularly C$\gamma$2, and C$\gamma$3) are responsible for antibody effector functions. In some mammals, for example in camels and llamas, full-length antibodies may consist of only two heavy chains, each heavy chain comprising immunoglobulin domains $V_H$, C$\gamma$2, and C$\gamma$3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to $V_H$, C$\gamma$1, C$\gamma$2, C$\gamma$3, $V_L$, and $C_L$.

Depending on the amino acid sequence of the constant domain of their heavy chains, intact antibodies can be assigned to different "classes." There are five-major classes (isotypes) of intact antibodies: IgA, IgD, IgE, IgG, and IgM, and several of these may be further divided into "subclasses," e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known to one skilled in the art. While some antibodies are monomeric, most are multimers. As is well-known in the art, the subunits of most multimeric antibodies are linked to each other via disulfide bonds. For example, human IgG is comprised of two light chains and two heavy chains, with the two heavy chains typically linked by two disulfide bonds in the hinge region and with each light chain linked to a different heavy chain via a disulfide bond.

An "antibody" (Ab) is a protein that binds specifically to a particular substance, known as an "antigen" (Ag) (see below). An "antibody" or "antigen-binding fragment" is an immunoglobulin that binds a specific "epitope." The term encompasses polyclonal, monoclonal, and chimeric antibodies (e.g., multispecific antibodies). In nature, antibodies are generally produced by lymphocytes in response to immune challenge, such as by infection or immunization. An "antibody combining site" is that structural portion of an antibody molecule comprised of heavy and light chain variable and hypervariable regions that specifically binds antigen.

The terms "antibody" or "antigen-binding fragment" respectively refer to intact molecules as well as functional fragments thereof, such as Fab, a scFv-Fc bivalent molecule, F(ab')$_2$, and Fv that are capable of specifically interacting with a desired target. In some embodiments, the antigen-binding fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains;

(5) Single chain antibody ("SCA"), a genetically engineered molecule containing the variable region of the light chain and the variable region of the heavy chain, linked by a suitable polypeptide linker as a genetically fused single chain molecule; and (6) scFv-Fc, is produced by fusing single-chain Fv (scFv) with a hinge region from an immunoglobulin (Ig) such as an IgG, and Fc regions.

In some embodiments, an antibody provided herein is a monoclonal antibody. In some embodiments, the antigen-binding fragment provided herein is a single chain Fv (scFv), a diabody, a tandem scFv, a scFv-Fc bivalent molecule, an Fab, Fab', Fv, F(ab')$_2$ or an antigen binding scaffold (e.g., affibody, monobody, anticalin, DARPin, Knottin, etc.).

An "antigen" (Ag) is any substance that reacts specifically with antibodies or T lymphocytes (T cells). An "antigen-binding site" is the part of an immunoglobulin molecule that specifically binds an antigen. Additionally, an antigen-binding site includes any such site on any antigen-binding molecule, including, but not limited to an MHC molecule or T cell receptor, but it can also include any substance against which an antibody or antigen-binding fragment has been raised, including artificially manufactured antigens and/or artificially manufactured antibodies or antigen-binding fragments.

The term "antigenic material" covers a substance that will elicit an innate or adaptive immune response. As used herein, "a portion of antigenic material" covers antigenic material or fragment thereof, which is capable of eliciting an innate or adaptive immune response, even if the fragment is an incomplete representation or subset of the antigenic material as a whole. It can include the minimal antigen sequence required to elicit a specific immune response.

An "epitope" or "antigenic determinant" is a structure, usually made up of, but not limited to, a short peptide sequence or oligosaccharide, that is specifically recognized or specifically bound by a component of the immune system. It is the site on an antigen recognized by an antibody.

An antibody or antigen-binding fragment to a specific "expansion target biomolecule" specifically interacts with at least some component of that "expansion target biomolecule."

An "immunogen" is a substance capable of eliciting an immune response. Each immunoglobulin molecule can potentially bind a variety of antibodies directed at its unique features, or "idiotype," which is comprised of a series of "idiotopes." An "idiotope" is a single antigenic determinant on a variable region of an antibody or T cell receptor. It is the set of idiotopes on an antibody which comprise the idiotype that makes that antibody unique. The "dominant idiotype" is the idiotype found on the major fraction of antibodies generated in response to an antigen.

As used herein, the terms "binds" or "binding" or grammatical equivalents, refer to compositions, directly or indirectly, having affinity for each other. "Specific binding" is where the binding is selective between two molecules. A particular example of specific binding is that which occurs between an antibody and an antigen. Typically, specific binding can be distinguished from non-specific when the dissociation constant ($K_D$) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding. "Affinity" is defined as the strength of the binding interaction of two molecules, such as an antigen and its antibody, which is defined for antibodies and other molecules with more than one binding site as the strength of binding of the ligand at one specified binding site. Although the noncovalent attachment of a ligand to antibody is typically not as strong as a covalent attachment, "high affinity" is for a ligand that binds to an antibody or other molecule having an affinity constant ($K_a$) of greater than $10^4$ $M^{-1}$, typically $10^5$-$10^{11}$ $M^{-1}$; as determined by inhibition ELISA or an equivalent affinity determined by comparable techniques, such as Scatchard plots or using $K_d$/dissociation constant, which is the reciprocal of the $K_a$, etc.

In one embodiment, the antibody, antigen-binding fragment, or affinity tag binds its target with a $K_D$ of 0.1 nM-10 mM. In one embodiment, the antibody, antigen-binding fragment, or affinity tag binds its target with a $K_D$ of 0.1 nM-1 mM. In one embodiment, the antibody, antigen-binding fragment, or affinity tag binds its target with a $K_D$ within the 0.1 nM range. In one embodiment, the antibody, antigen-binding fragment, or affinity tag binds its target with a $K_D$ of 0.1-2 nM. In another embodiment, the antibody, antigen-binding fragment, or affinity tag binds its target with a $K_D$ of 0.1-1 nM. In another embodiment, the antibody, antigen-binding fragment, or affinity tag binds its target with a $K_D$ of 0.05-1 nM. In another embodiment, the antibody, antigen-binding fragment, or affinity tag binds its target with a $K_D$ of 0.1-0.5 nM. In another embodiment, the antibody, antigen-binding fragment, or affinity tag its target with a $K_D$ of 0.1-0.2 nM. In some embodiments, the antibody, antigen-binding fragment, or affinity tag bind its target directly. In some embodiments, the antibody, antigen-binding fragment, or affinity tag bind its target indirectly, for example, the antibody, antigen-binding fragment, or affinity tag is a secondary antibody that binds to an antibody bound to the target. "Specificity" refers to the ability of an antibody to discriminate between antigenic determinants. It also refers to the precise determinants recognized by a particular receptor or antibody. "Specificity" may be affected by the conditions under which the discrimination or recognition takes place (e.g., pH, temperature, salt concentration, and other factors known in the art).

A "peptide" is a compound of two or more subunit amino acids, amino acid analogs, or peptidomimetics. The subunits may be linked by peptide bonds or by other bonds (e.g., as esters, ethers, and the like). While the term "protein" encompasses the term "polypeptide," a "polypeptide" may be less than a full-length protein. However, the terms "polypeptide" and "protein" are used herein interchangeably and refer to any polymer of amino acids (dipeptide or greater) linked through peptide bods or modified peptide bonds. Thus, the terms "polypeptide" and "protein" include oligopeptides, protein fragments, fusion proteins, and the like. It should be appreciate that the terms "polypeptide" and "protein" can include moieties such as lipoproteins and glycoproteins, except where the context dictates otherwise.

A "tag peptide sequence" is a short peptide or polypeptide chain of 3 or more amino acids, which is attached to an antibody or other protein or moiety of interest. In some embodiments, a polypeptide, protein, or chimeric protein comprises a tag polypeptide sequence, which is used for purification, detection, labeling or some other function, such as by specific binding to an antibody. The antibody may be in solution or bound to a surface. The tag peptide sequence should not interfere with the function of the rest of the polypeptide, protein, or chimeric protein. Examples of tag proteins are well-known to those of ordinary skill in the art.

Probes and Labels

The word "label" as used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition, which is detectable.

As used herein, the term "probe" refers to synthetic or biologically produced nucleic acids that are designed to contain specific nucleotide sequences which hybridize under stringent conditions to target nucleic acid sequences. Conditions, such as pH, temperature, salt concentration, and other factors known in the art, may be varied to effect "hybridization" of one nucleic acid domain to another (see, e.g., Wetmur, "DNA Probes: Applications of the Principles of Nucleic Acid Hybridization," *Critical Reviews in Biochemistry and Molecular Biology* 26(3/4): 227-259 (1991)).

As used herein, a "labeled probe," "antibody operably linked to a label," "antibody operably linked to a detectable label," "antigen-binding fragment operably linked to a label," antigen-binding fragment operably linked to a detectable label," "nucleic acid probe operably linked to a detectable label," or "nucleic acid strand operably linked to a detectable label" refer to a probe which is prepared with a marker moiety, "label" or "detectable label" for detection. The marker moiety should be linked in a place and manner so as not to interfere with, significantly/substantially decrease or inhibit, the binding or affinity of the probe to the target. For example, with respect to an antibody (or antigen-binding protein) operably linked to a label, the label should be attached to the antibody (or antigen-binding fragment) in such a manner as to prevent the label from inhibiting binding of the antibody (or antigen-binding fragment) to its expansion target biomolecule. With respect to an antibody, the marker moiety is preferably attached to a constant region of the antibody, probably to a Cγ2 or a Cγ3 region of a heavy chain. With respect to an antigen-binding fragment, the marker moiety is preferably attached to a constant region of the antigen-binding fragment. Alternatively, the label and/or the gel binding moiety is preferably operably linked at the location of one or more disulfide linkages with the antibody. With respect to a nucleic acid, the marker moiety is attached at either the 5' end, the 3' end, internally, or a suitable combination thereof. The preferred marker moiety is an identifying label, preferably a detectable label. In some embodiments, the detectable label is a fluorophore. In some embodiments, one probe may be attached to multiple marker moieties. In some embodiments, multiple types of probes are used, each type having a different marker moiety. The labeled probe may also be comprised of a plurality of different nucleic acid sequences and/or antibodies (or antigen-binding fragments) each labeled with one or more marker moieties. Each of the marker moieties may be the same or different. It may be beneficial to label the different probes (e.g., nucleic acid sequences, antibodies or antigen-binding fragments) each with a different marker moiety. This can be accomplished by having a single distinguishable moiety on each probe. For example, probe A may be attached to moiety X and probe B may be attached to moiety Y. Alternatively, probe A may be attached to moieties X and Y while probe B may be attached to moiety Z and W. As another alternative, probe A may be attached to moieties X and Y while probe B may be attached to moieties Y and Z. All the probes "A" and "B" described above would be distinguishable and uniquely labeled.

"Acrylates" or "polyacrylates" are a family of polymers made from acrylate monomers, which are esters having vinyl groups. Acrylate monomers include, but are not limited to acrylamide, N-isopropylacrylamide, dimethylacrylamide, acrylic acid, methacrylic acid, hydroxyl ethyl acrylamide, or oligo(ethylene glycol) methyl ether methacrylate, which can polymerize. For example, free radical polymerization of an acrylate monomer solution comprising sodium acrylate, acrylamide and N—N'-methylenebisacrylamide can be induced by the addition of ammonium persulfate (APS) initiator and tetramethylethylenediamine (TEMED).

In some embodiments, the antibody or antigen-binding fragment can be acrylated directly, making it suitable for polymerization. This process can be performed either before, after, or simultaneously with attachment of the detectable label (e.g., a fluorophore). The most straightforward way to acrylate antibodies is to use a reagent which can react with the many amino groups present on its surface such as the commercially available Acryoyl-X SE, 6-((acryloyl)amino)hexanoic acid, succinimidyl ester (Acryoyl-X, ThermoFisher A20770). Once the polymerizable group is presented on the surface of the antibody, free radical polymerization in its presence will result with it being attached to the polymer gel.

Direct acrylation of the antibody or antigen-binding fragment yields a "gel binding moiety" operably linked to the antibody or antigen-binding fragment. In some embodiments, the gel binding moiety is a acrylamide, methacrylamide, acrylate, or methacrylate group. For example, the reagent is Acryoyl-X SE, 6-((acryloyl)amino)hexanoic acid, succinimidyl ester (Acryoyl-X, ThermoFisher A20770).

During free radical polymerization of the acrylate monomers (above), the "gel binding moiety" is covalently conjugated to the polyelectrolyte gel, thereby indirectly attaching the labeled antibody or antigen-binding fragment to the resulting polyelectrolyte gel. The "gel binding moiety" should be linked to the antibody or antigen-binding fragment in a place and manner so as not to interfere with, significantly/substantially decrease or inhibit, the binding or affinity of the probe to the target and also so as not to interfere with, significantly/substantially decrease or inhibit, the detection of the marker moiety. For example, with respect to an antibody (or antigen-binding protein) operably linked to a gel binding moiety, the gel binding moiety should be attached to the antibody (or antigen-binding fragment) in such a manner as to prevent the gel binding moiety from inhibiting binding of the antibody (or antigen-binding fragment) to its expansion target biomolecule and should also be attached to the antibody (or antigen-binding fragment) in such a manner as to prevent the gel binding moiety from inhibiting detection of the label. With respect to an antibody, gel binding moiety is preferably attached to a constant region of the antibody, probably to a Cγ2 or a Cγ3 region of a heavy chain. With respect to an antigen-binding fragment, the gel binding moiety is preferably attached to a constant region of the antigen-binding fragment. In some embodiments, the modified antibody comprises an antibody modified with a fluorophore operably linked to a constant region on one heavy chain and a gel binding moiety operably linked to a constant region on the other heavy chain.

In some embodiments, pyridazinediones (PD), such as a dibromopyridazinedione (diBrPD), which contain both the acrylate group and the dye, can be inserted into one or more of the disulfide linkage(s) within the antibody. (See, e.g., Maruani et al., Nature Commun. 6:6645 [DOI: 10/1038/ncomms7645]). With this approach, the number and location of modification sites are controlled, the solubility of the antibody undergoes little or no alteration, and the reagents maintain the structural stability of the disulfide bond.

Samples

"Biological sample" includes samples of organs, tissues, cells, blood, fluid, or other materials obtained from a biological organism. It also includes a biological organism, a cell, virus, or other replicative entity. Also included are solid cultures (including bacterial or tissue cultures). Also included are solid sample, including, but not limited to non-biological solids containing a biological organism, cell, virus, or other replicative entity; organs; tissues; cells; or sections (e.g., sagittal sections, cross-sections, and the like), washings, homogenizations, sonications, and similar treatments of biological samples. A biological sample may be obtained directly from a biological organism (e.g., a human or non-human animal, a plant, a fungus, a yeast, a protist, a bacterium or algae), it may be from a culture, or it may initially be attached to a non-biological solid. A biological sample may include a cancerous or noncancerous tumor or other growth, including a noncancerous aberrant growth.

A "physiological condition" of a biological organism may be normal or abnormal. The physiological condition may result from the genetic make-up of the organism (including, but not limited to, the expression of various proteins), from environmental factors (including, but not limited to, the ingestion of drugs, poisons, food, and beverages and the exposure of an organism to toxic or non-toxic substances), from disease (both infectious or non-infectious), from an injury, from a metabolic disorder, from pregnancy or nursing, and from a wide range of other circumstances, including genetic diseases, syndromes, and polymorphisms with respect to the genotype and/or phenotype of the organism, organ, tumor, tissue, or cell.

By "tissue sample" is meant a collection of similar cells obtained from a tissue of a subject or patient, preferably containing nucleated cells with chromosomal material. The four main human tissues are (1) epithelium; (2) the connective tissues, including blood vessels, bone and cartilage; (3) muscle tissue; and (4) nerve tissue. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. The tissue sample may contain compounds which are not naturally intermixed with the tissue in nature such as preservatives, anticoagulants, buffers, fixatives, nutrients, antibiotics, or the like.

For the purposes herein, a "section" of a tissue sample is meant a single part or piece of a tissue sample, e.g., a thin slice of tissue or cells cut from a tissue sample. It is understood that multiple sections of tissue samples may be taken and subjected to analysis. Types of sections include sagittal sections and cross-sections and may be individual or serial.

Alternatively, "whole mounts" may be studied. "Whole mounts" include, but are not limited to, an organ or an organism.

As used herein, "cell line" refers to a permanently established cell culture that will proliferate given appropriate fresh medium and space. In some embodiments, a cell line can be cultured and expanded to form a layer of cells, such as an adherent layer of cells, over the bottom of a plate or over the bottom of a well, such as a well of a multiwell plate.

The term "subject" refers to an organism, including a mammal (including a human) in need of therapy for, or susceptible to, a condition or its sequelae. The subject may include dogs, cats, pigs, cows, sheep, goats, horses, rats, and mice and humans. The term "subject" does not exclude an individual that is normal in all respects.

"Vertebrates" include fish, reptiles, amphibians, birds (avians), and mammals. "Mammals" include, but are not limited to, murines, simians, humans, farm animals, sport animals, and pets. Mammals may be egg-laying, or they may be marsupials or placentals. "Birds" include, but are not limited to, farm animals, sport animals, and pets.

Cross-Linking Groups for Protein Conjugation

Cross-linking groups are categorized based on their chemical reactivities and other properties (see Chemistry of Crosslinking, Thermo Fisher Scientific, https://www.thermofisher.com/us/en/home/life-science/protein-biology/protein-biology-learning-center/protein-biology-resource-library/pierce-protein-methods/chemistry-crosslinking.html). Cross-linking groups for protein conjugation include, but are not limited to, carboxyl-to-amine reactive groups (e.g., carbodiimide, EDC/EDAC, DCC, N-hydroxysuccinimide [NHS], sulfo-N-hydroxysuccinimide [sulfo-NHS], amine-biotin reagents), amine-reactive groups (e.g., NHS ester, sulfo-NHS ester, sulfotetraflurophenyl-STP, imidoester, pentafluorophenyl ester, hydroxymethyl phosphine), sulfhydryl-reactive groups (e.g., maleimide, haloacetyle [bromo-, iodo-], pyridyldisulfide, thiosulfonate, vinylsulfone), aldehyde-reactive groups (i.e., oxidized sugars/carbonyls; e.g., hydrazide, aldoxyamine), photoreactive groups (i.e., nonselective/random insertion; e.g., diazirine, aryl azide), chemoselective ligation groups (e.g., Staudinger reagent pairs), and hydroxyl (nonaqueous)-reactive groups (e.g., isocyanate). Typically, cross-linking groups are selected based on factors including chemical specificity, spacer arm length, water-solubility, cell membrane permeability, and/or presence of spontaneously reactive or photoreactive groups. They may be homobifunctional (i.e., having identical reactive groups at each end of a spacer arm [e.g., disuccinimidyl suberate (DSS)]) or heterobifunctional (i.e., having different reactive groups at each end of a spacer arm [e.g., sulfosuccinimidyl-4-(N-maleimidomethyl)cyclohexane-1-carboxylate (sulfo-SMCC)]).

Carbodiimides, including N-hydroxysuccinimide (NHS) and sulfo-N-hydroxysuccinimide (sulfo-NHS), are zero-length crosslinkers resulting in direct conjugation of carobxylates (—COOH) to primary amines (—$NH_2$) without becoming part of the final crosslining amide bond between the target molecules. Sulfo-NHS is a water soluble analog of NHS.

NHS-esters are reactive groups formed by activation of carboxylate molecules. Frequently, they react with primary amines in mildly alkaline conditions (pH 7.2-8.5), resulting in stable amide bonds and releasing N-hydroxysuccinimide, which is removed, e.g., by dialysis or desalting. Sulfo-NHS esters contain a sulfonate (—$SO_3$) group on the N-hydroxysuccinimide ring. Their hydrophilicity inhibits their permeation of cell membranes and allows them to be used for cell surface applications.

Labeling of biomolecules can be performed using activated esters, such as N-hydroxysuccinimide (NHS—) esters and other activated esters (including, but not limited to, sulfo-NHS, sulfotetrafluorophenyl-STP, imidoesters). These reactive compounds can be used for the modification of primary amine groups (—$NH_2$). Modifications can include fluorescent labels, fluorescence quenchers, and other reporter groups. Some embodiments include the attachment of an alkyne group or azido group. Activated esters can be used to modify proteins and peptides, as well as amino-oligonucleotides, amino-modified DNA, and amino-containing sugars. With respect to peptides and proteins, these groups are found at the N-terminus of each polypeptide chain or in the side-chain of lysine (Lys, K) amino acid residues. Because they are usually positively charged at physiological pH, peptide or protein configuration at physiological pH would typically place them on the outside surface of the tertiary structure, and their nucleophilic character would make them targets for conjugation.

Solvents for labeling can include, but are not limited to, water, dimethyl sulfoxide (DMSO), or dimethyl formamide (DMF). Non-sulfonated NHS-esters may need to be dissolved in a water-miscible organic solvent (e.g., DMSO, DMF) prior to addition to a reaction mixture, while sulfo-NHS esters are more water soluble. Preferably, reactions buffers, such as phosphate-buffered saline (PBS) are used that do not contain primary amines, while buffers with primary amines (e.g., Tris, glycine) can be used as quenching buffers.

The dibenzocyclooctyne group (DBCO; azadibenzocyclooctyne [ADIBO]; dibenzoazacyclooctyne [DIBAC]) is a cycloalkyne that is thermally stable and has a high specific reactivity toward azide groups through strain-promoted click chemistry reaction (Cu(I)-free Strain-Promoted Alkyne-Azide Click Chemistry [SPAAC]) in the absence of a catalyst (e.g., copper) or reducing agents (e.g., DTT) (See Prim et al., ADIBO-Based "Click" Chemistry for Diagnostic Peptide Micro-Array Fabrication: Physicochemical and Assay Characteristics, *Molecules* [2013] 18: 9833.) Ligation occurs quickly and can yield stable triazoles. At physiological pH, the DBCO group does not react with amines or hydroxyls. Dibenzocyclooctyne-N-hydroxysuccinimide ester (DBCO-NHS ester) has a 6-carbon spacer arm, which holds the DBCO moiety close to the tagged molecule, and a terminal carboxylic acid activated as NHS ester, which can react with free amine groups to form a stable amide bond. It interacts with primary amines (N-terminus or lysine side chain) or with aminosilane-coated surfaces. DBCO can be used to label oligomers and other nucleotides at the 5' end.

DBCO-containing modification reagents include, but are not limited to, dibenzylcyclooctyne acids (e.g., dibenzylcyclooctyne acid [DBCO acid], DBCO-lc-acid, dibenzylcyloocctyne —C6-acid); dibenzylcyclooctyne amines (e.g., dibenzylcyclooctyne amine [DBCO amine]); dibenzylcyclooctyne-N-hydroxysuccinimide esters (dibenzylcyclooctyne-N-hydroxysuccinimide ester [DBCO-NHS-ester]; dibenzylcyclooctyne-sulfo-N-hydroxysuccinimide ester [DBCO-sulfo-NHS-ester]; DBCO-lc-NIH ester; dibenzylcyclooctyne-C6-NHS ester [DBCO-C6-NHS ester]; sulfo-dibenzylcyclooctyne-NHS-ester sodium salt [sulfo-DBCO-NHS-ester sodium salt]; dibenzylcyclooctyne-polyethylene glyco14-N-hydroxysuccinimide ester [DBCO-PEG4-NHS ester]; dibenzylcyclooctyne-PEG4-NHS ester; dibenzylcyclooctyne-S—S—NHS ester [DBCO-S—S—NHS ester]);

dibenzylcyclooctyne melimides (e.g., dibenzylcyclooctyne-maleimide [DBCO-maleimide]); and dibenzylcyclooctyne-polyethylene glycol-4-maleimides (dibenzylcyclooctyne-polyethylene glycol-4-maleimide [DBCO-PEG4-maleimide]).

Detection Methods

In various aspects, provided herein are methods of detecting or locating a target in a biological sample. Targets are detected by contacting a biological sample with a target detection reagent, e.g., a single-stranded nucleic acid or a fragment thereof, and a labeling reagent. The presence or absence of targets are detected by the presence or absence of the labeling reagent, and the location of the labeling reagent indicates where the target biomolecules were located. In some instances, the biological sample is contacted with the target detection reagent and the labeling reagent concurrently e.g., the detection reagent is a primary antibody and the labeling reagent is a fluorescent dye both of which are conjugated to a single nucleic acid strand. Alternatively, the biological sample is contacted with the target detection reagent and the labeling reagent sequentially, e.g., the detection reagent is a primary antibody and the labeling reagent includes a secondary antibody. For example, the biological sample is incubated with the detection reagent, in some cases together with the labeling reagent, under conditions that allow a complex between the detection reagent (and labeling reagent) and target to form. After complex formation the biological sample is optionally washed one or more times to remove unbound detection reagent (and labeling reagent). When the biological sample is further contacted with a labeling reagent that specifically binds the detection reagent that is bound to the target, the biological sample can optionally be washed one or more times to remove unbound labeling reagent. The presence or absence of the target, and if present its location, in the biological sample is then determined by detecting the labeling reagent.

Imaging technologies for transcriptional profiling of expanded complex tissues include, but are not limited to, confocal microscopy or super-resolution microscopy of RNA in situ hybridization targets, e.g., via ExM in combination with RNA fluorescence in situ hybridization (FISH) and RNA hybridization chain reaction (HCR), as described above.

The methods described herein provide for the detection of multiple targets in a sample.

Multiple targets are identified by contacting the biological sample with additional detection reagents followed by additional labeling reagent specific for the additional detection reagents using the methods described above. For example, each target is associated with a probe comprising a single-stranded nucleic acid (e.g., DNA) with a sequence specific or barcode for that target RNA of interest (e.g., an mRNA). The probes optionally comprises a detectable label. To detect multiple targets simultaneously, a plurality of probes, each recognizing a corresponding unique sequence of one or more RNA targets of interest. The plurality of probes can be added sequentially (with removal of the previous priors prior to addition of the next one) or simultaneously. Alternatively, a different probe can be added to each distinct well in an array on a multiwell format plate or to each spot on a microarray.

HCR is conducted with first and second nucleic acid hairpin molecules (e.g., single-stranded DNA) at least one of which has a detectable label. In some cases, sets or subsets of labeled hairpin molecules are prepared with distinct labels, e.g., fluorophores that are distinguished by their emission spectra, e.g., one that emits in the green spectra and one that emits in the red spectra. The pairs (sets) of labeled hairpin molecules can then be added simultaneously to a biological sample to detect multiple targets at once. Alternatively, sets or subsets of labeled hairpin molecules are prepared with the same label. Each set of the labeled hairpin molecules can then be added sequentially to detect a specific target, with each set of labeled hairpin molecules removed from the biological sample prior to adding the next set of labeled hairpin molecules to detect multiple targets sequentially.

The detection moiety, i.e., detectable label, is a substance used to facilitate identification and/or quantitation of a target. Detection moieties are directly observed or measured or indirectly observed or measured. Detection moieties include, but are not limited to, radiolabels that can be measured with radiation-counting devices; pigments, dyes or other chromogens that can be visually observed or measured with a spectrophotometer; spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems, for example. The detection moiety can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The detection moiety may also take the form of a chemical or biochemical, or an inert particle, including but not limited to colloidal gold, microspheres, quantum dots, or inorganic crystals such as nanocrystals or phosphors. The term detection moiety or detectable label can also refer to a "tag" or hapten that can bind selectively to a labeled molecule such that the labeled molecule, when added subsequently, is used to generate a detectable signal. For instance, one can use biotin, iminobiotin or desthiobiotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex Red or Amplex Gold (Molecular Probes, Inc.) to detect the presence of HRP Similarly, the tag can be a hapten or antigen (e.g., digoxigenin), and an enzymatically, fluorescently, or radioactively labeled antibody can be used to bind to the tag. Numerous labels are known by those of skill in the art and include, but are not limited to, particles, fluorescent dyes, haptens, enzymes and their chromogenic, fluorogenic, and chemiluminescent substrates, and other.

A fluorophore is a chemical moiety that exhibits an absorption maximum beyond 280 nm, and when covalently attached in a labeling reagent retains its spectral properties. Fluorophores include, without limitation; a pyrene, an anthracene, a naphthalene, an acridine, a stilbene, an indole or benzoindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a borapolyazaindacene, a xanthene, an oxazine or a benzoxazine, a carbazine, a phenalenone, a coumarin, a benzofuran and benzphenalenone and derivatives thereof. As used herein, oxazines include resorufins, aminooxazinones, diaminooxazines, and their benzo-substituted analogs.

When the fluorophore is a xanthene, the fluorophore may be a fluorescein, a rhodol, or a rhodamine. As used herein, fluorescein includes benzo- or dibenzofluoresceins, seminaphthofluoresceins, or naphthofluoresceins. Similarly, as used herein rhodol includes seminaphthorhodafluors. Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position. Fluorophores include xanthene (rhodol, rhodamine, fluorescein and derivatives thereof) coumarin, cyanine, pyrene, oxazine and borapolyazaindacene. In addition, the fluorophore can be sulfonated xanthenes, fluorinated xanthenes, sulfonated coumarins, fluorinated coumarins and sulfonated cyanines. The choice of the fluorophore in the labeling reagent will determine the absorption and fluorescence emission properties of the labeling reagent. Physical properties of a fluorophore label include spectral characteristics (absorption, emission and stokes shift), fluorescence intensity, lifetime, polarization and photo-bleaching rate all of which can be used to distinguish one fluorophore from another.

Typically, a fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

Preferably the detection moiety is a fluorescent dye. Fluorescent dyes include, for example, Fluorescein, Rhodamine, Texas Red, Cy2, Cy3, Cy5, Cy0, Cy0.5, Cy1, Cy1.5, Cy3.5, Cy7, VECTOR Red, ELF™ (Enzyme-Labeled Fluorescence), FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-(6-(7-nitrobenz-2-oxa-1,3-diazol-4-yl)amino)caproyl) (NBD), BODIPY™, boron dipyrromethene difluoride, Oregon Green, MITOTRACKER™ Red, DiOC7 (3), DilC18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

Many fluorophores can also function as chromophores.

In addition to fluorophores, enzymes also find use as detectable moieties. Enzymes are desirable detectable moieties because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. This is advantageous where there is a low quantity of target present in the sample or a fluorophore does not exist that will give comparable or stronger signal than the enzyme. However, fluorophores are most preferred because they do not require additional assay steps and thus reduce the overall time required to complete an assay. The enzyme substrate is selected to yield the preferred measurable product, e.g. colorimetric, fluorescent or chemiluminescence. Such substrates are extensively used in the art.

A preferred colorimetric or fluorogenic substrate and enzyme combination uses oxidoreductases such as horseradish peroxidase and a substrate such as 3,3'-diaminobenzidine (DAB) and 3-amino-9-ethylcarbazol-e (AEC), which yield a distinguishing color (brown and red, respectively). Other colorimetric oxidoreductase substrates that yield detectable products include, but are not limited to, 2,2-azino-bis(3-ethylbenzothiaz-oline-6-sulfonic acid) (ABTS), o-phenylenediamine (OPD), 3,3',5,5'-tetramethylbenzidine (TMB), o-dianisidine, 5-amino salicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplexe Red reagent and its variants and reduced dihydroxanthenes, including dihydrofluoresceins and dihydrorhodamines including dihydrorhodamine 123. Peroxidase substrates that are tyramides represent a unique class of peroxidase substrates in that they can be intrinsically detectable before action of the enzyme but are "fixed in place" by the action of a peroxidase in a process described as tyramide signal amplification (TSA). These substrates are extensively utilized to label targets in samples that are cells, tissues, arrays, or microarrays for their subsequent detection by microscopy, flow cytometry, optical scanning and fluorometry.

Additional colorimetric (and in some cases fluorogenic) substrate and enzyme combination use a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy4-methylcoumarinyl phosphate (DiFMUP) fluorescein diphosphate, 3-0-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates.

Glycosidases, in particular β-galactosidase, β-glucuronidase and β-glucosidase, are additional suitable enzymes. Appropriate colorimetric substrates include, but are not limited to, 5-bromo4-chloro-3-indolyl β-D-galactopyranoside (X-gal) and similar indolyl galactosides, glucosides, and glucuronides, o-nitrophenyl β-D-galactopyranoside (ONPG) and p-nitrophenyl β-D-galactopyranosid-e. Preferred fluorogenic substrates include resorufin β-D-galactopyranoside, fluorescein digalactoside (FDG), fluorescein diglucuronide and their structural variants, 4-methylumbelliferyl β-D-galactopyranoside, carboxyumbelliferyl β-D-galactopyranoside and fluorinated coumarin β-D-galactopyranosides.

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

For example, the enzyme is luciferase or aequorin. The substrates are luciferine, ATP, $Ca^{++}$ and coelenterazine.

In addition to enzymes, haptens such as biotin are useful detectable moieties. Biotin is useful because it can function in an enzyme system to further amplify a detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, or nucleotides.

In some cases, a detectable moiety is a fluorescent protein. Exemplary fluorescent proteins include green fluorescent protein (GFP), the phycobiliproteins and the derivatives thereof, luciferase or aequorin. The fluorescent proteins, especially phycobiliprotein, are particularly useful for creating tandem dye labeled labeling reagents. These tandem dyes comprise a fluorescent protein and a fluorophore for the purposes of obtaining a larger stokes shift where the emission spectra is farther shifted from the wavelength of the fluorescent protein's absorption spectra. This is particularly advantageous for detecting a low quantity of a target in a sample where the emitted fluorescent light is maximally optimized, in other words little to none of the emitted light is reabsorbed by the fluorescent protein. For this to work, the fluorescent protein and fluorophore function as an energy transfer pair where the fluorescent protein emits at the wavelength that the fluorophore absorbs at and the fluorophore then emits at a wavelength farther from the fluorescent proteins than could have been obtained with only the fluorescent protein. A particularly useful combination is phycobiliproteins and sulforhodamine fluorophores, or the sulfonated cyanine fluorophores; or the sulfonated xanthene derivatives. Alternatively, the fluorophore functions as the energy donor and the fluorescent protein is the energy acceptor.

Methods of Visualizing the Detection Moiety Depend on the Label.

In some cases, the sample is illuminated with a light wavelength selected to give a detectable optical response, and observed with means for detecting the optical response. Equipment that is useful for illuminating fluorescent compounds described herein includes, but is not limited to, hand-held ultraviolet lamps, mercury arc lamps, xenon lamps, lasers and laser diodes. These illumination sources are optically integrated into laser scanners, fluorescent microplate readers or standard or microfluorometers. The degree and/or location of signal, compared with a standard or expected response, indicates whether and to what degree the sample possesses a given characteristic or desired target.

The optical response is optionally detected by visual inspection, or by use of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

When an indirectly detectable label is used then the step of illuminating typically includes the addition of a reagent that facilitates a detectable signal such as colorimetric enzyme substrate. Radioisotopes are also considered indirectly detectable wherein an additional reagent is not required but instead the radioisotope must be exposed to X-ray film or some other mechanism for recording and measuring the radioisotope signal. This can also be true for some chemiluminescent signals that are best observed after expose to film.

As used herein, "specificity" refers to the ability of an antibody to discriminate between antigenic determinants. It also refers to the determinants recognized by a particular receptor or antibody. It also refers to the ability of a receptor to discriminate between substrates, such as drugs. With respect to nucleic acids, it refers to identity or complementarity as a function of competition or recognition/binding, respectively. "Specificity" of recognition or binding may be affected by the conditions under which the recognition or binding takes place (e.g., pH, temperature, salt concentration, and other factors known in the art).

An "effective amount" is an amount sufficient to affect beneficial or desired results. An effective amount may be administered one or more times to achieve the beneficial or desired result.

As used in the specification and claims, the singular forms "a," "an," and "the" include plural references unless the context dictates otherwise. For example, the term "a molecule" can also include a plurality of molecules.

When not otherwise stated, "substantially" means "being largely, but not wholly, that which is specified." The term "about" or "approximately" means within an acceptable error range for the particular value as determined by one of ordinary skill in the art, which will depend in part on how the value is measured or determined, i.e., limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1%, and still more preferably ±0.1% from the specified value, as such variations are appropriate to perform the disclosed methods.

EXAMPLES

Materials and Methods

Antibody staining, Polymerization and Expansion: Brain slices taken from the cryo-protectant solution were washed with 1×PBS and blocked with blocking buffer (5% normal donkey serum and 0.1% TritonX-100 in 1×PBS) for 2 hours at room temperature or overnight at 4° C. Slices were incubated with respective primary and secondary antibodies for 6 hours at room temperature (RT) or overnight at 4° C. Upon washing with 1×PBS after each antibody incubation, slices were washed with MOPs buffer for 30 minutes, then incubated in a solution of anchoring reagents Acryloyl-X (6-((acryloyl)amino)hexanoic acid succinimidyl ester; 100 µg/mL) and NucliX (FIG. 3A;100 µg/mL) in MOPs buffer for 6 hours or overnight at room temperature. Anchoring reagent solution was removed and slices were washed with 1×PBS three times. Then slices were incubated in monomer solution for 10 minutes with rocking at RT. Polymerization was initiated by adding initiator (10% APS) and accelerator (10% TMED) reagents and incubated at room temperature for 2 hours. Once the polymerization completed tissue-gel composite was transferred into a Bind-Silane treated glass bottom 6 well plate and subjected to digestion with Proteinase K in digestion buffer for overnight at room temperature with rocking. Digestion buffer was removed and gels were expanded by washing with cell culture grade water for 4 times 30 minutes each.

Gel Embedding in Polyacrylamide gel Matrix: Prepare embedding solution by mixing 3% acrylamide, 0.15% N,N'-Methylenebisacrylamide in 5 mM Tris or Borate buffer and adjust the pH to 10.5. Then add the embedding solution, 10% APS and 10% TMED to the expanded gel and incubate on a rocker for 15 minutes. Remove the embedding solution and repeat one more times. Then remove the embedding solution and place an appropriately cut glass slide on top of the gel and incubate at 37° C. for 2 hours.

Multiplexed in situ Hybridization: Re-embedded gel was incubated in wash buffer for 30 minutes at room temperature. Wash buffer was removed and 1 nM of initiator probe (Though 'n'' number of initiator probes can be used, we have used 3 probes per hybridization cycle) solution prepared in hybridization buffer was added and the gel was incubated at 37° C. for at least 18 hours. Hybridization buffer with initiator probe was removed and gel was washed wash buffer twice (60 minutes each at 37° C.). Wash buffer was removed and gel was washed with 1×PBS for 2 hours at 37° C. and PBS wash was repeated at room temperature instead of 37° C. 1×PBS was removed and gel was incubated with amplification buffer for 30 minutes at room temperature for pre-amplification. To prepare fluorescently labeled hairpin solution, each HCR hairpin was subjected to snap cooling procedure. In snap cooling procedure each hairpin was heated at 95° C. for 90 seconds, and cooled to room temperature on the benchtop for 30 minutes. Then hairpin solution (60 nM) was prepared by adding all snap-cooled hairpins to amplification buffer at room temperature. Amplification buffer was removed and fresh prepared hairpin solution was added to the gel and incubated for 2-4 hours at room temperature. To stop amplification hairpin solution was removed and gel was washed with 5×SSCT buffer 4 times with 30 minutes incubation each time. Gels were stained with DAPI (100 ng/μL) in water for 15 minutes. Gel is ready to image at this point, Andor Revolution Spinning Disk Confocal microscope was used for imaging. Gels were stored in 0.05×SSC buffer 4° C.

Probe removal by DNAse I digestion: To remove the probes and prepare the gel/specimen for next round of in situ hybridization with next set of probes, 0.05×SSC buffer was removed and gels were incubated with 0.25 U/μL of DNAse I in Reaction Buffer for at least 6 hours to overnight at 37° C. DNAse I was removed and the gel was washed with 1×PBS and stored in 1×PBS at 4° C. until imaging. Images were collected using Andor Revolution Spinning Disk Confocal microscope, then gel/specimen was proceeded with next round of in situ hybridization of next set of probes.

Bind-Silane treatment: Prepare Bind-Silane solution by mixing 5 μL of Bind-Silane, 8 mL of ethanol, 1.8 mL of nuclease free water and 0.2 mL of acetic acid in a falcon tube. Then add 1 mL Bind-silane solution to each well of glass bottom 6 well plate and incubate for 10 minutes at room temperature. Remove Bind-silane solution and let air dry for 10 minutes, wash twice with EtOH and let air dry for 30-60 minutes.

Sectioning and storing the Tissue: Mice approximately 8 weeks of age were euthanized by carbon dioxide asphyxiation and transcardially perfused with 1×PBS followed by 4% paraformaldehyde. Brains harvested and incubated in 4% paraformaldehyde overnight. Brains were washed with 1×PBS and incubated in a solution of 30% Sucrose, 100 mM Glycine in 1×PBS at 4° C. for 48 hours. Once the brains were shrunk to the bottom of the tube, they were embedded by flash freezing in OCT. Then brains were sectioned on a cryostat with 50 μM size of each slice and stored in cryo-protectant solution (30% ethylene glycol+30 Sucrose+1×PBS) at −20° C. until staining.

Figure 1B:
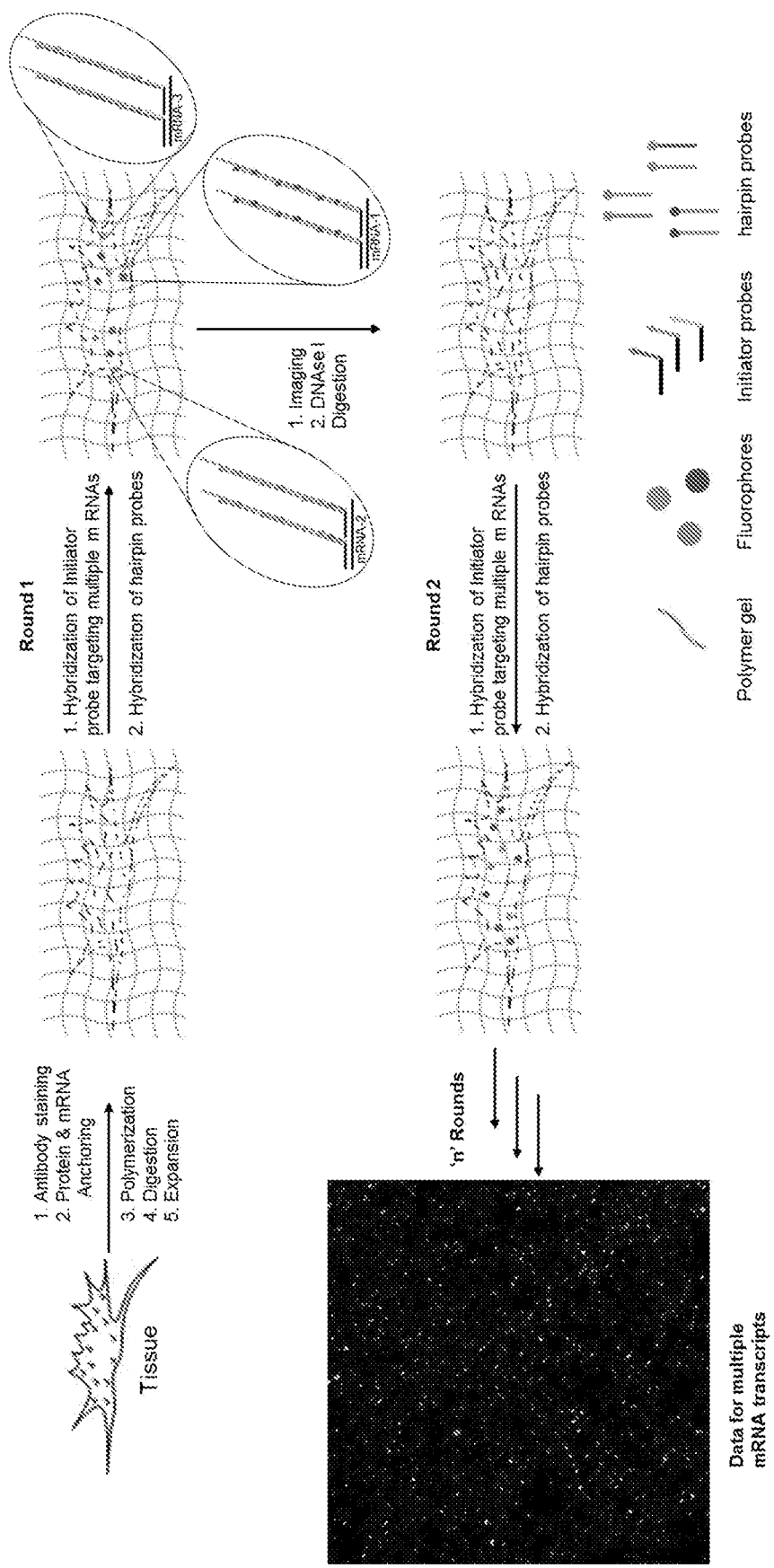
Figure 2:
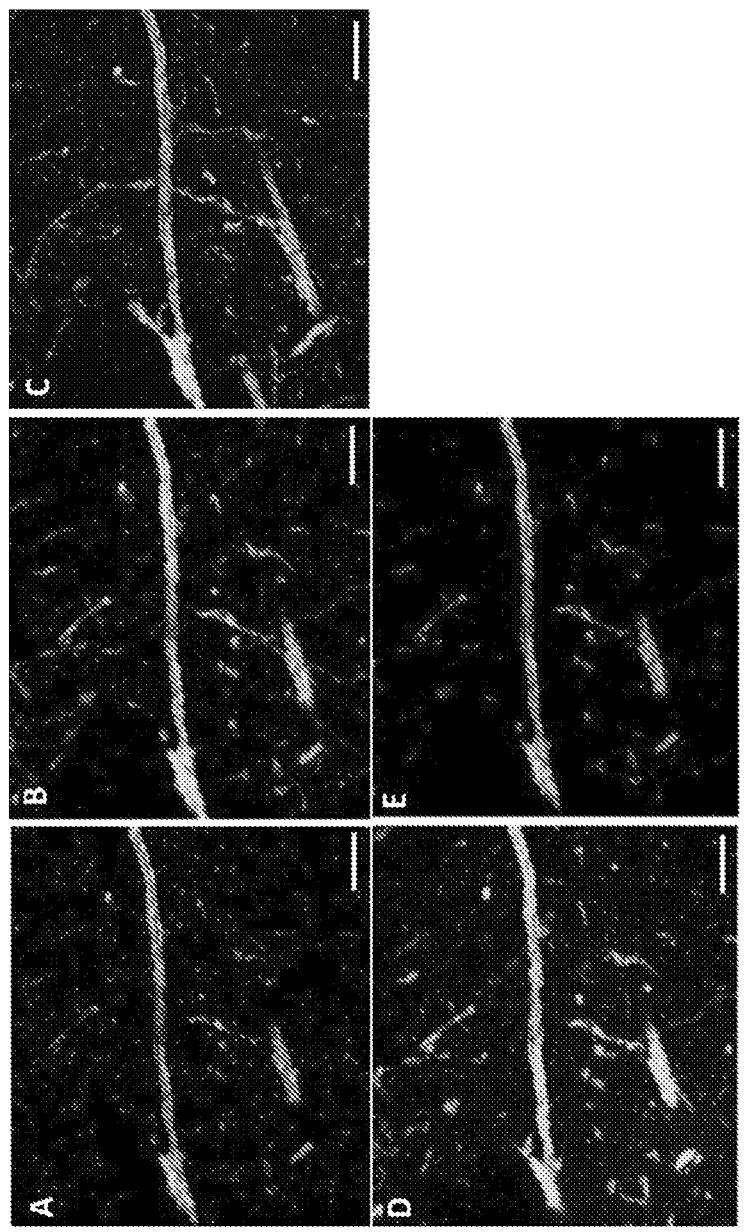
FIGS. 2A-2E. In situ hybridization of multiple RNA transcripts (one transcript per cycle) for multiple cycles. Photographs showing a neuron dendrite (green: stained for with parvalbumin antibody) from a mouse brain hippocampal region with the results of serially hybridized RNA probes as follows: (A) Camk2a, (B) Dlg4, (C) Gad1, (D) Camk2a (a second hybridization with Camk2a), and (E) Probes removed with DNAse I for each cycle after imaging.

Example 1. As shown in FIGS. 1A and 1B, a biological sample of interest is obtained, and stained with primary and secondary antibodies. Under RNAse-free conditions, the RNA in the sample is linked, directly or indirectly, to a gel binding moiety. The sample is then contacted with a solution comprising monomers of a polyelectrolyte gel, which are then polymerized by free radical polymerization to form the polyelectrolyte gel, as well as anchoring the protein and/or to the gel. The sample is digested, and the gel is dialyzed to expand it, optionally followed by polyacrylamide embedding and imaging. The next step is probe hybridization, HCR amplification, followed by washing, imaging, and digestion with DNAse I. Subsequent rounds of probe, hybridization, HCR amplification, washing, imaging, and DNAse digestion are conducted.

Example 2. More specifically, for an RNA target of interest (e.g., an mRNA), a single-stranded DNA probe is provided having a 5' sequence including a complementary or partially complementary to a sequence of the RNA target of interest, and a 3' HCR initiator domain having a first initiator segment and a 3' second initiator segment. The probe is optionally also operably linked to a detectable label. The expanded sample is contacted with the DNA probe under conditions to selectively hybridize with the RNA target of interest. If the probe includes a detectable label, an image may be taken of the gel.

An HCR amplifier is provided. The HCR amplifier comprises a first DNA hairpin molecule and a second DNA hairpin molecule, which coexist metastably in the absence of the probes hybridized to the RNA target of interest. The first DNA hairpin molecule sequentially comprises (i) a first domain comprising a 5' tail complementary or partially complementary to the 3' second initiator segment of the 3' HCR intiator domain of the probe, (ii) a second domain complementary or partially complementary to the first initiator segment of the 3' HCR initiator domain of the probe, (iii) a third domain, and (iv) a fourth domain complementary or partially complementary to the first domain. The second DNA hairpin molecule sequentially comprises (i) a first domain comprising a 5' domain complementary or partially complementary to the second domain of said first DNA hairpin molecule, (ii) a second domain complementary or partially complementary to the first domain of said first DNA hairpin molecule, (iii) a third domain complementary or partially complementary to the first domain of the second DNA hairpin molecule, and (iv) a fourth domain comprising a 3' tail complementary or partially complementary to the third domain of the first DNA hairpin molecule. One or both of the first or second DNA hairpin molecules is operably linked to a detectable label, such as a fluorophore.

The gel is contacted with the HCR amplifier (first and second DNA hairpin molecules) under conditions in which (a) the 3' second initiator segment of the 3' HCR initiator domain of the probe selectively hybridizes to the first domain of said first DNA hairpin molecule, initiating a hybridization chain reaction, (b) the second domain of the first DNA hairpin molecule hybridizes to the first initiator segment of the 3' HCR initiator domain of the probe, exposing the third domain of the first DNA hairpin molecule, and (c) wherein the third domain of the first DNA hairpin molecule hybridizes to the fourth domain of the second DNA hairpin molecule exposing the second domain of the second DNA hairpin molecule and the first domain of the second DNA hairpin molecule.

Additional first and second DNA hairpin molecules are hybridized, resulting in a series of extensions, each with at least one additional detectable label (two if both the first and second DNA hairpin molecules comprise detectable label(s)).

The detectable label is detected, and the results are imaged. Optionally, the gel is treated with DNAse I, and subsequent rounds of hybridization, washing, imaging, and DNAse digestion are conducted.

Example 3. For an RNA target of interest (e.g., an mRNA) in a biological sample of interest, and a plurality of unique single-stranded DNA probes are provided. Each unique probe has a 5' sequence complementary or partially complementary to a unique sequence of mRNA target of interest, and a 3' HCR initiator domain having a first initiator segment and a 3' second initiator segment The probes are optionally also operably linked to a detectable label. The expanded sample is contacted with the DNA probes under conditions to selectively hybridize with the RNA targets of interest. If the probes include a detectable label, an image may be taken of the gel.

An HCR amplifier is provided. The HCR amplifier comprises a first DNA hairpin molecule and a second DNA hairpin molecule, which coexist metastably in the absence of the probes hybridized to the RNA target of interest. The first DNA hairpin molecule sequentially comprises (i) a first domain comprising a 5' tail complementary or partially complementary to the 3' second initiator segment of the 3' HCR initiator domain of the probes, (ii) a second domain complementary or partially complementary to the first initiator segment of the 3' HCR initiator domain of the probes, (iii) a third domain, and (iv) a fourth domain complementary or partially complementary to the first domain. The second DNA hairpin molecule sequentially comprises (i) a first domain comprising a 5' domain complementary or partially complementary to the second domain of said first DNA hairpin molecule, (ii) a second domain complementary or partially complementary to the first domain of said first DNA hairpin molecule, (iii) a third domain complementary or partially complementary to the first domain of the second DNA hairpin molecule, and (iv) a fourth domain comprising a 3' tail complementary or partially complementary to the third domain of the first DNA hairpin molecule. One or both of the first or second DNA hairpin molecules is operably linked to a detectable label.

The gel is contacted with the HCR amplifier (first and second DNA hairpin molecules) under conditions in which (a) the 3' second initiator segment of the 3' HCR initiator domain of each of the probes selectively hybridizes to a first domain of a first DNA hairpin molecule, initiating a hybridization chain reaction, (b) the second domain of the first DNA hairpin molecule hybridizes to the first initiator segment of the 3' HCR initiator domain of the probes, exposing the third domain of the first DNA hairpin molecule, and (c) wherein the third domain of the first DNA hairpin molecule hybridizes to the fourth domain of the second DNA hairpin molecule exposing the second domain of the second DNA hairpin molecule and the first domain of the second DNA hairpin molecule.

Additional first and second DNA hairpin molecules are hybridized, resulting in a series of extensions, each with at least one additional detectable label (two if both the first and second DNA hairpin molecules comprise detectable label(s)).

The detectable label is detected, and the results are imaged. Optionally, the gel is treated with DNAse I, and subsequent rounds of hybridization, washing, imaging, and DNAse digestion are conducted.

Example 4. For a plurality of RNA targets of interest (e.g., a plurality of mRNAs) in a biological sample of interest, A plurality of unique single-stranded DNA provided are provided. Each unique DNA probe has a 5' sequence complementary or partially complementary to a unique domain sequence of one of the RNA targets of interest, and a 3' HCR initiator domain having a first initiator segment and a 3' second initiator segment. The probe is optionally also operably linked to a detectable label. The expanded sample is contacted with the DNA probes under conditions to selectively hybridize with the RNA targets of interest. If the probe includes a detectable label, an image may be taken of the gel.

A plurality of unique HCR amplifiers is provided. Each unique HCR amplifier corresponds to a unique probe and comprises a unique first DNA hairpin molecule and a unique second DNA hairpin molecule, which coexist metastably in the absence of the probes hybridized to the RNA targets of interest. Each unique first DNA hairpin molecule sequentially comprises (i) a first domain comprising a 5' tail complementary or partially complementary to the 3' second initiator segment of the 3' HCR initiator domain of the corresponding probe, (ii) a second domain complementary or partially complementary to the first initiator segment of the 3' HCR initiator domain of that probe, (iii) a third domain, and (iv) a fourth domain complementary or partially complementary to the first domain. The second DNA hairpin molecule sequentially comprises (i) a first domain comprising a 5' domain complementary or partially complementary to the second domain of said first DNA hairpin molecule, (ii) a second domain complementary or partially complementary to the first domain of said first DNA hairpin molecule, (iii) a third domain complementary or partially complementary to the first domain of the second DNA hairpin molecule, and (iv) a fourth domain comprising a 3' tail complementary or partially complementary to the third domain of the first DNA hairpin molecule. One or both of the unique first or second DNA hairpin molecules is operably linked to a unique detectable label.

The gel is contacted with the plurality of HCR amplifiers (unique first and second DNA hairpin molecules) under conditions in which, with respect to each unique first and second nucleic acid hairpin molecules of each unique HCR amplifier, (a) the 3' second initiator segment of the 3' HCR initiator domain of each of the corresponding probes selectively hybridizes to a first domain of a first DNA hairpin molecule, initiating a hybridization chain reaction, (b) the second domain of the first DNA hairpin molecule hybridizes to the first initiator segment of the 3' HCR initiator domain of the probe, exposing the third domain of the first DNA hairpin molecule, and (c) wherein the third domain of the first DNA hairpin molecule hybridizes to the fourth domain of the second DNA hairpin molecule exposing the second domain of the second DNA hairpin molecule and the first domain of the second DNA hairpin molecule.

Additional unique first and second DNA hairpin molecules are hybridized, resulting in a series of extensions, each with at least one additional detectable label (two if both the first and second DNA hairpin molecules comprise detectable label(s)).

Each unique detectable label is detected, and the results are imaged. Optionally, the gel is treated with DNAse I, and subsequent rounds of hybridization, washing, imaging, and DNAse digestion are conducted.

Example 5. In situ hybridization of multiple RNA transcripts (one transcript per cycle) for multiple cycles. As shown in FIGS. 2A-2E, a neuron dendrite (green: stained for with parvalbumin antibody) from a mouse brain hippocampal region with the results of serially hybridized RNA (red) probes as follows: (A) Camk2a, (B) Dlg4, (C) Gad1, (D) Camk2a (a second hybridization with Camk2a), and (E) Probes removed with DNAse I for each cycle after imaging.

Figure 3A:
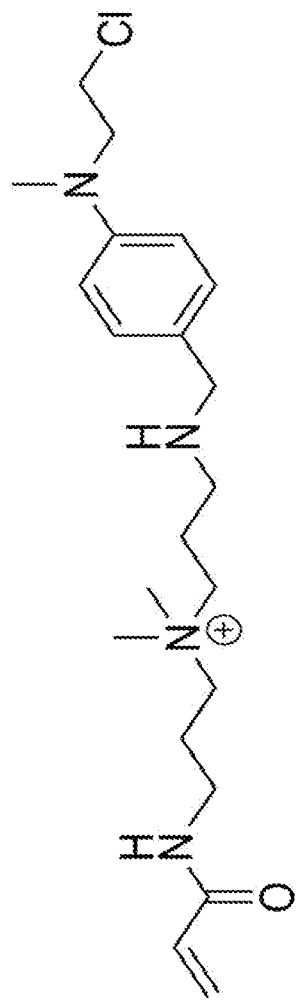
FIGS. 3A-3B. Figures depicting (A) the structural details of NucliX and (B) a synthetic scheme for NucliX.
Figure 3B:
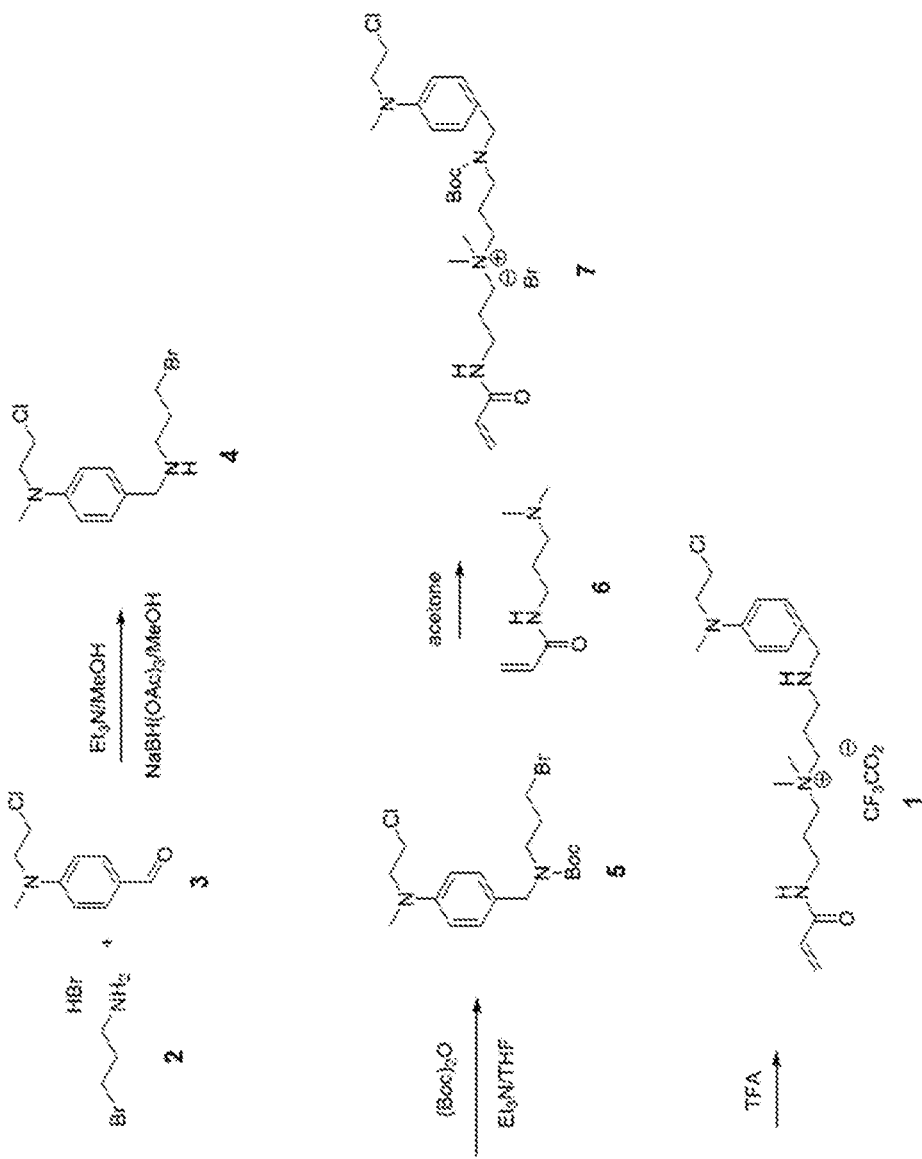
Figure 4:
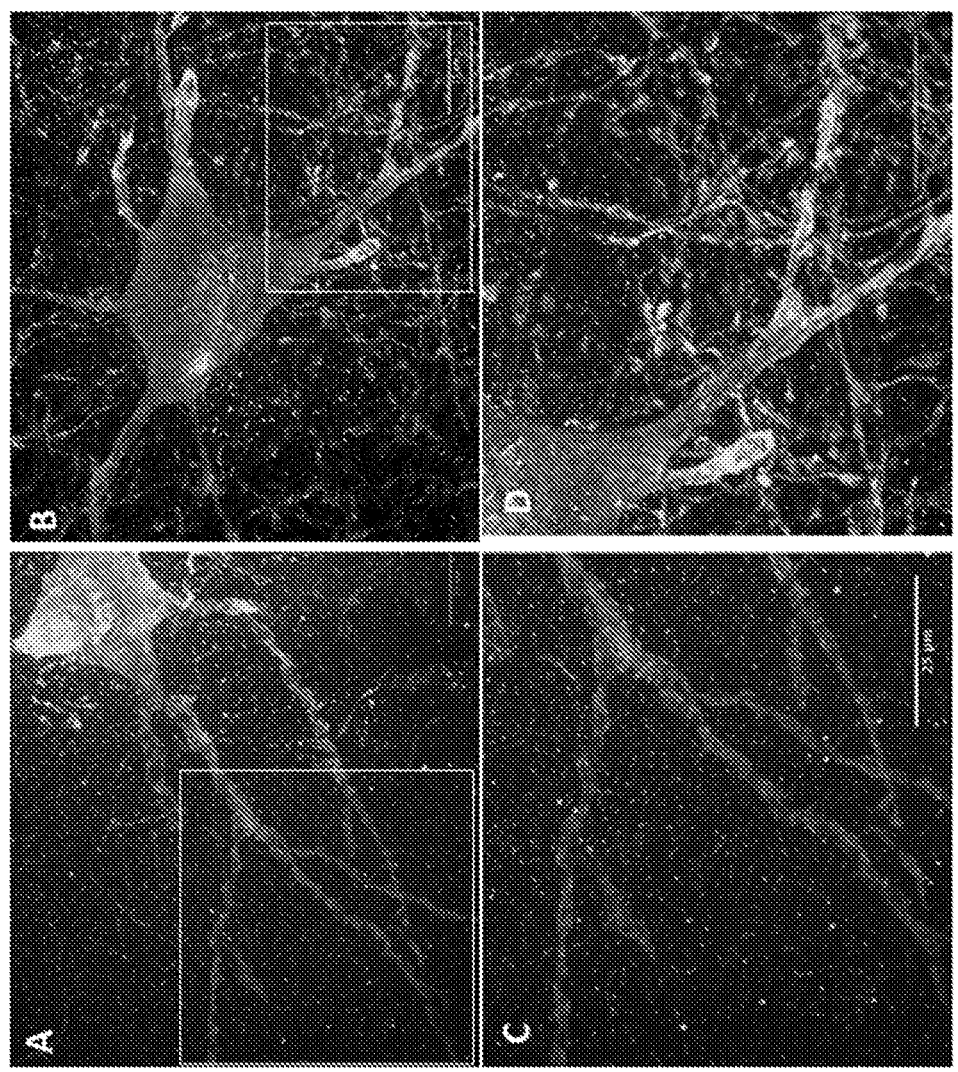
FIGS. 4A-4D. NucliX, nucleic acid anchoring reagent works as well as LabelX (see Chen et al., Nat. Meth. 13:679 [2016]). Photographs showing results of RNA-FISH of actin mRNA on a mouse brain hippocampus stained with parvalbumin (green) anchored using (A) Acryloyl-X (see Tillberg et al., Nat. Biotech. 34 (9):987 [2016]) and LabelX molecules, or (B) Acryloyl-X and NucliX molecules. Details of the staining can be seen as enlargements in (C) boxed region of FIG. 4A, treated with Acryloyl-X and LabelX and in (D) boxed region of FIG. 4B, treated with Acryloyl-X and NucliX.

Example 6. NucliX, nucleic acid anchoring reagent works as well as LabelX. As shown in FIGS. 4A-4D, results of RNA-FISH of actin mRNA on a mouse brain hippocampus stained with parvalbumin (green) anchored using (A) Acryloyl-X and LabelX molecules (B) Acryloyl-X and NucliX molecules. (structural details of and synthesis for NucliX are shown in FIGS. 3A and 3B, respectively) Details of the staining can be seen as enlargements in (C) boxed region of FIG. 4A, treated with Acryloyl-X and LabelX and in (D) boxed region of FIG. 4B, treated with Acryloyl-X and NucliX.

Figure 5:
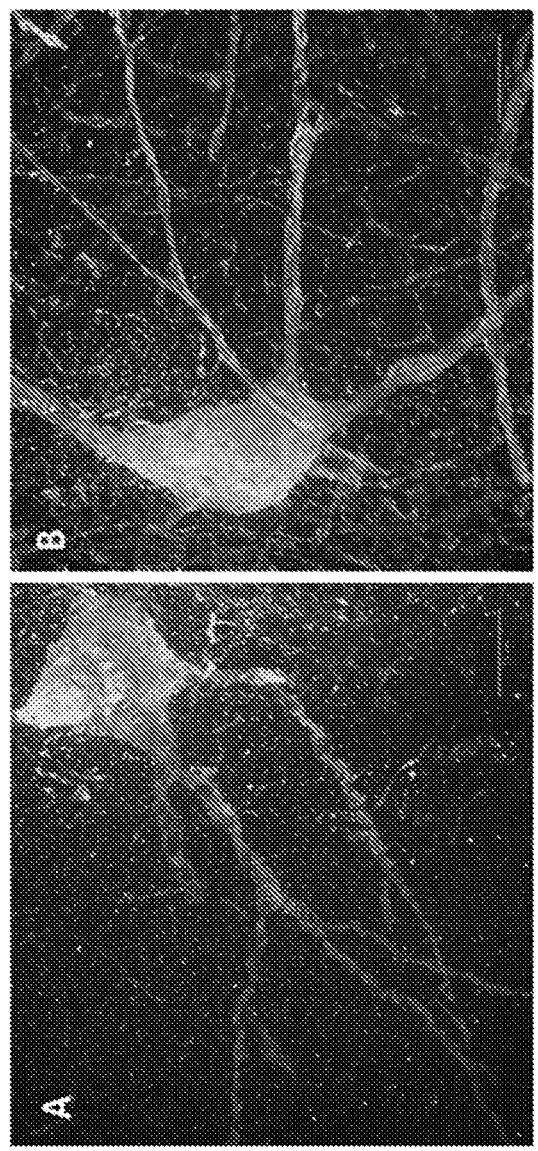
FIGS. 5A-5B. Number of initiator probes for target RNA can be reduced. Photographs showing results of RNA-FISH of actin mRNA (red) on a mouse brain hippocampus stained for parvalbumin (green) with (A) 24 Initiator probes targeting actin mRNA or (B) 5 Initiator probes targeting actin mRNA.
Figure 6:
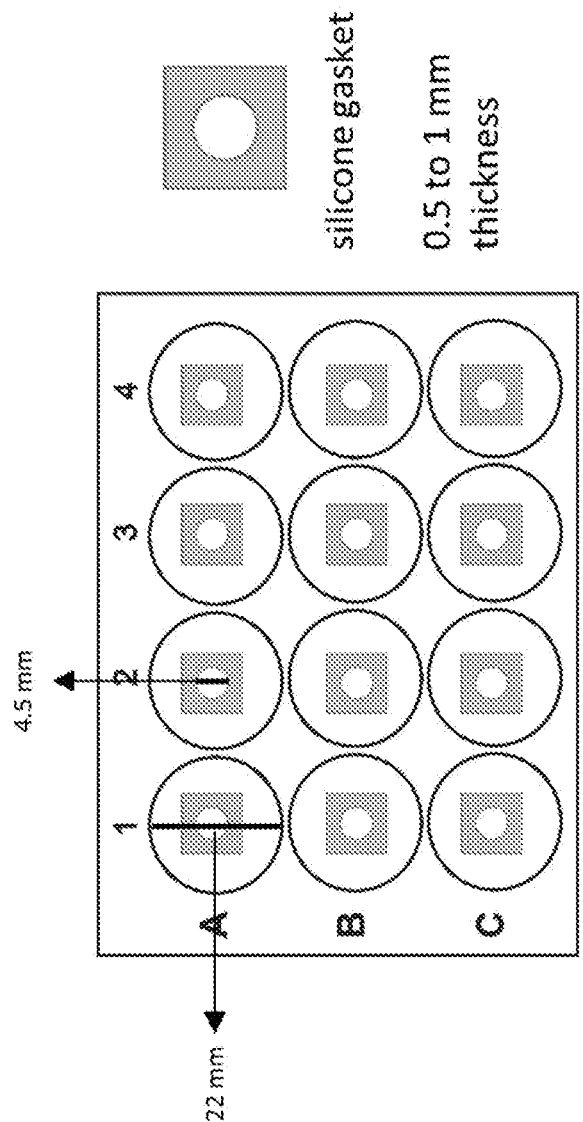
FIG. 6. Schematic depiction of expansion microscopy high-throughput format design using 12 well plate.
Figure 7:
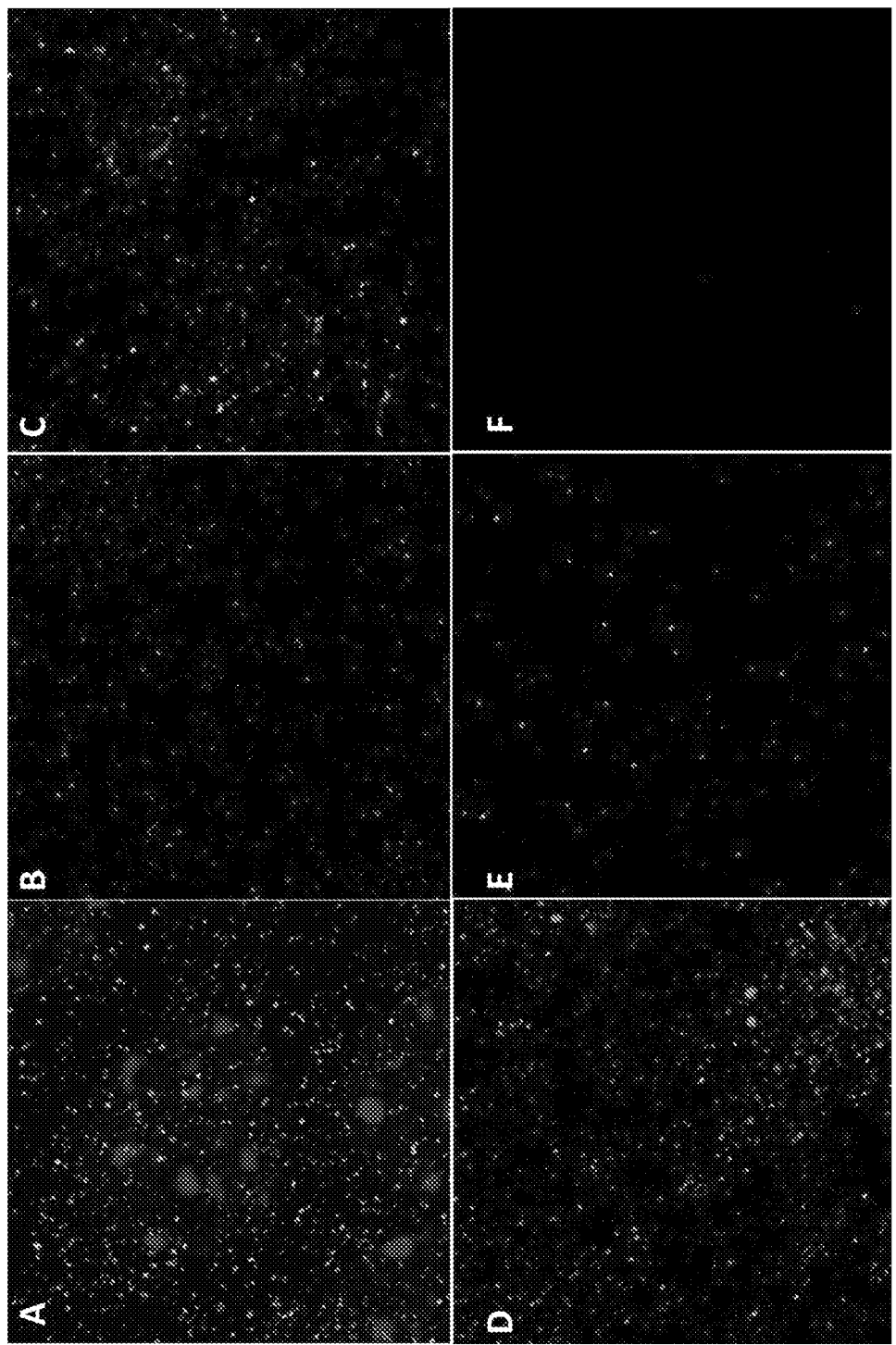
FIG. 7. In situ hybridization of multiple RNA transcripts per cycle for multiple cycles. Photographs showing a DAPI stained (blue) mouse brain hippocampal region with the results of serially hybridized RNA probes (three transcripts per cycle) as follows: (A) Nucleus (DAPI, blue), Map2 (green), Camk2a (red), Gfap (purple) (B) Gad1 (green), STUB1 (red), DOHH (purple) (C) Asic (green), Cnr1 (red), Rbfox3 (purple) (D) Tubb3 (green), Dlg4 (red), Olig2 (purple) (E) NF1 (green), Kcnj3 (red), Chrm3 (purple) (F) Probes removed with DNAse I for each cycle after imaging.

Example 7. Number of initiator probes for target RNA can be reduced. As shown in FIGS. 5A and 5B, results of RNA-FISH of actin mRNA (red) on a mouse brain hippocampus stained for parvalbumin (green) with (A) 24 DNA probes complementary to the RNA target of interest or (B) 5 Initiator probes complementary to the RNA target of interest. An automated 12-well multiwell plate high-throughput format was used (FIG. 6).

Example 8. In situ hybridization of multiple RNA transcripts per cycle for multiple cycles. As shown in FIGS. 7A to 7F, a DAPI stained (blue) mouse brain hippocampal region with the results of serially hybridized RNA probes (three transcripts per cycle) as follows: (A) Nucleus (DAPI, blue), Map2 (green), Camk2a (red), Gfap (purple) (B) Gad1 (green), STUB1 (red), DOHH (purple) (C) Asic (green), Cnr1 (red), Rbfox3 (purple) (D) Tubb3 (green), Dlg4 (red), Olig2 (purple) (E) NF1 (green), Kcnj3 (red), Chrm3 (purple) (F) Probes removed with DNAse I for each cycle after imaging.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of detecting different nucleic acids in a biological sample, said method comprising:
   (a) contacting the different nucleic acids in the sample with a first gel binding moiety under conditions such that the first gel binding moiety operably links to the different nucleic acids in the sample and forms first gel binding moiety-nucleic acids;
   (b) contacting the first gel binding moiety-nucleic acids with a solution comprising monomers of a polyelectrolyte gel, thereby forming a mixture comprising the first gel binding moiety-nucleic acids and the monomers of a polyelectrolyte gel;
   (c) forming said polyelectrolyte gel by polymerizing said monomers and producing a gel composition by covalently conjugating the first gel binding moiety of the first gel binding moiety-nucleic acids in the mixture to said polyelectrolyte gel;
   (d) proteolytically digesting said gel composition;
   (e) after step (d), producing an expanded polyelectrolyte gel comprising the first gel binding moiety-nucleic acids by dialyzing said gel composition;
   (f) providing a plurality of different initiator nucleic acid probes targeting the different nucleic acid acids in the biological sample, wherein each of the plurality of different initiator nucleic acid probes comprise (A) a sequence complementary to a sequence from one of the different nucleic acids, and (B) a hybridization chain reaction (HCR) initiator sequence; and each of the plurality of initiator nucleic acid probes comprises a pair of fluorophore-labeled DNA hairpins that metastably co-exist in the absence of one of the plurality of different initiator nucleic acid probes;
   (g) contacting the first gel binding moiety-nucleic acids of said expanded polyelectrolyte gel in said gel composition with one of the plurality of different initiator nucleic acid probes under conditions suitable for performing a HCR such that a fluorescent amplification polymer is formed on said expanded polyelectrolyte gel in said gel composition by a HCR, wherein, during the process of the HCR, after the sequence from the one of the different nucleic acids hybridizes to one hairpin of the pair of the fluorophore-labeled nucleotide hairpins from the one of the different initiator nucleic acid probes, the one hairpin of the pair of the fluorophore-labeled nucleotide hairpins from the one of the different initiator nucleic acid probes is assembled with another hairpin of the pair of the fluorophore-labeled nucleotide hairpins from the one of the different initiator nucleic acid probes;
   (h) detecting the one of the different nucleic acids by detecting a fluorescent image from the fluorescent amplification polymer on said expanded polyelectrolyte gel in said gel composition;
   (i) after step (h), removing the one of the plurality of different initiator nucleic acid probes that has not been incorporated into the fluorescent amplification polymer and the fluorescent amplification polymer on said expanded polyelectrolyte gel from said gel composition; and
   (j) repeating steps (g) to (i) for multiple times using a different initiator nucleic acid probe from the plurality of different initiator nucleic acid probes, in each of the multiple times, producing a different fluorescent amplification polymer on said expanded polyelectrolyte gel in said gel composition, and detecting a different nucleic acid from the different nucleic acids in the biological sample by detecting a different fluorescent image from the different fluorescent amplification polymer on said expanded polyelectrolyte gel in said gel composition, wherein the different initiator nucleic acid probe from the plurality of different initiator nucleic acid probes hybridizes to the different nucleic acid from the different nucleic acids in the biological sample, and wherein the first gel binding moiety comprises

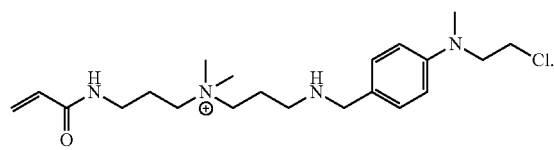 [SMILES: C=CC(=O)NCCC[N+](C)(C)CCCNCc1ccc(N(C)CCCl)cc1]

2. The method of claim 1, wherein the first gel binding moiety has an acryloyl or a methacryloyl group.

3. The method of claim 1, step (a) further comprising contacting proteins in the sample with a second gel binding moiety under conditions such that the second gel binding moiety operably links to the proteins and forms second gel binding moiety-proteins after step (a), and the second gel binding moiety of the second gel binding moiety-proteins is covalently conjugated to the polyelectrolyte gel after step (c).

4. The method of claim 3, further comprising, prior to step (a), the steps:
contacting the sample with at least one primary antibody under conditions such that the at least one primary antibody selectively recognizes a protein in the biological sample; and
contacting the sample with at least one secondary antibody operably linked to a detectable label.

5. The method of claim 1, the removing step is performed by washing away the one of the plurality of different initiator nucleic acid probes that has not been incorporated into the fluorescent amplification polymer and the fluorescent amplification polymer on said expanded polyelectrolyte gel from said gel composition.

6. The method of claim 1, further comprising, between step (e) and step (f), a step for embedding the expanded polyelectrolyte gel comprising the first gel binding moiety-nucleic acids in a polyacrylamide gel matrix.

7. The method of claim 1, further comprising, prior to step (f), obtaining an image of the expanded polyelectrolyte gel comprising the first gel binding moiety-nucleic acids.

8. The method of claim 7, wherein the image is obtained using a confocal microscopy.

9. The method of claim 1, wherein the plurality of different nucleic acids comprise ribonucleic acid (RNA).

10. The method of claim 9 wherein the RNA is mRNA.

11. The method of claim 1, wherein the pair of the fluorophore-labeled DNA hairpins is labeled with a fluorophore selected from the group consisting of fluorescein isothiocyanate (FITC), tetramethylrhodamine (TRITC), 4',6-diamidino-2-phenylindole (DAPI), and cyanine dye 5 (Cy5).

12. The method of claim 1, wherein each hairpin of the pair of fluorophore-labeled nucleotide hairpins in each of the plurality of different initiator nucleic acid probes is labeled with the same fluorophore.

13. The method of claim 1, wherein said biological sample is chemically fixed and permeabilized prior to step (a).

14. The method of claim 1, wherein the dialyzing step comprises dialyzing said gel composition in water.

15. The method of claim 1, wherein said biological sample is derived from a vertebrate.

16. The method of 15, wherein the vertebrate is a mammal.

17. The method of claim 16, wherein the mammal is a human.

18. The method of claim 1, wherein said biological sample is a brain sample, a heart sample, a lung sample, a gastrointestinal sample, a sample from a circulatory system, a kidney sample, a urogenital sample, a pancreatic sample, a gall bladder sample, a muscle sample, a breast sample, a glandular sample, or a bone sample.

19. The method of claim 1, wherein the method can be used for detecting different nucleic acids in a plurality of biological samples.

20. The method of claim 19, wherein the plurality of biological samples are on an array or on a microarray.

21. The method of claim 20, wherein the array comprises a multiwell plate and each of said plurality of biological samples is in a separate well of said multiwell plate.

22. The method of claim 19, wherein the plurality of biological samples comprises serial sections from a single organism.

23. The method of claim 22 wherein the method is performed under RNAse-free conditions.

24. The method of claim 1, wherein the different nucleic acids are RNA, the plurality of different initiator nucleic acid probes are DNA and the removing step comprises
treating said gel composition with a deoxyribonuclease.

25. The method according to claim 24, wherein the deoxyribonuclease is DNAse I.

26. The method according to claim 24, further comprising a step for washing said gel composition after step (j).

27. The method of claim 3, wherein the second gel binding moiety is 6-((acryloylamino)hexanoic acid succinimidyl ester.

28. The method of claim 3, wherein the second gel binding moiety has an acryloyl or a methacryloyl group.

29. The method of claim 1, wherein each hairpin of the pair of fluorophore-labeled nucleotide hairpins in each of the plurality of different initiator nucleic acid probes is labeled with a different fluorophore.

30. A compound having the structure:

31. A method for operably linking a nucleic acid in a sample to a polyelectrolyte gel comprising generating a complex comprising the nucleic acid and the compound of claim 30, forming a mixture by contacting the complex in the sample with monomers of a polyelectrolyte gel, and producing a polyelectrolyte gel by polymerizing the monomers in the mixture, thereby operably linking the nucleic acid in the sample to the polyelectrolyte gel by covalently conjugating the compound of claim 30 in the complex to the polyelectrolyte gel.

* * * * *